United States Patent
Sojka et al.

(10) Patent No.: US 10,533,009 B2
(45) Date of Patent: *Jan. 14, 2020

(54) METHOD OF STABILIZING RIBOFLAVIN

(71) Applicant: ELC Management LLC, Melville, NY (US)

(72) Inventors: Milan Franz Sojka, Coram, NY (US); Kerri Stanganelli, Williston Park, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,795

(22) Filed: Jun. 21, 2018

(65) Prior Publication Data

US 2018/0319802 A1 Nov. 8, 2018

Related U.S. Application Data

(63) Continuation of application No. 14/664,418, filed on Mar. 20, 2015, now Pat. No. 10,030,022.

(51) Int. Cl.
 *C07D 475/14* (2006.01)
 *C08B 37/08* (2006.01)
 (Continued)

(52) U.S. Cl.
 CPC .......... *C07D 475/14* (2013.01); *A61K 8/0241* (2013.01); *A61K 8/0279* (2013.01); *A61K 8/673* (2013.01); *A61K 8/735* (2013.01); *A61Q 1/02* (2013.01); *C08B 37/0072* (2013.01); *C08J 3/24* (2013.01); *A61K 2800/434* (2013.01)

(58) Field of Classification Search
 CPC .............. A61K 8/673; A61K 2800/434; C07D 475/14; A61Q 1/02
 See application file for complete search history.

(56) References Cited

U.S. PATENT DOCUMENTS 6,093,411 A * 7/2000 Bissett ..................... A61K 8/35
 424/401
6,117,435 A 9/2000 Painter et al.
(Continued)

FOREIGN PATENT DOCUMENTS

FR 2991990 A1 * 12/2013 ............. A61K 8/585
JP 2003-516954 5/2003
(Continued)

OTHER PUBLICATIONS

Sharez et al. Journal of Organic Chemistry vol. 10, 1999-2012 (Year: 2014).*

(Continued)

*Primary Examiner* — Mark S Kaucher
(74) *Attorney, Agent, or Firm* — Peter Giancana

(57) ABSTRACT

A method of stabilizing riboflavin by affixing the riboflavin to at least one substrate for the riboflavin by covalent bonding, hydrogen bonding, Van der Waals forces, or a combination thereof, to form an optically-activated complex, is provided. When activated by absorption of light in the ultraviolet (UV) to visible region of the electromagnetic spectrum the riboflavin in the complex re-emits light of longer wavelength in the blue-green-yellow region of the electromagnetic spectrum.

7 Claims, 16 Drawing Sheets

(51) Int. Cl.
*A61K 8/02* (2006.01)
*A61K 8/67* (2006.01)
*A61Q 1/02* (2006.01)
*A61K 8/73* (2006.01)
*C08J 3/24* (2006.01)

(56) References Cited

U.S. PATENT DOCUMENTS

| | | | |
|---|---|---|---|
| 7,306,809 | B2 | 12/2007 | Sojka et al. |
| 7,780,955 | B2 | 8/2010 | Cassin |
| 9,545,371 | B2 * | 1/2017 | Sojka ............... A61K 8/735 |
| 9,962,565 | B2 * | 5/2018 | Sojka ............... A61K 8/60 |
| 10,030,022 | B2 * | 7/2018 | Sojka ............... C07D 475/14 |
| 2002/0192248 | A1 | 12/2002 | Victor |
| 2002/0192260 | A1 | 12/2002 | Victor |
| 2003/0103924 | A1 | 6/2003 | Reinehr et al. |
| 2003/0170189 | A1 | 9/2003 | Victor |
| 2004/0052742 | A1 * | 3/2004 | Sojka ............... A61K 8/11 424/63 |
| 2005/0074417 | A1 * | 4/2005 | Chen ............... B08B 9/0555 424/63 |
| 2007/0183992 | A1 | 8/2007 | Dumousseaux et al. |
| 2011/0260110 | A1 | 10/2011 | Mikami |
| 2013/0095157 | A1 | 4/2013 | Jeong et al. |
| 2015/0110842 | A1 | 4/2015 | Jeanne-Rose |
| 2016/0271264 | A1 * | 9/2016 | Sojka ............... A61K 8/60 |

FOREIGN PATENT DOCUMENTS

| | | |
|---|---|---|
| JP | 2004-217739 | 8/2004 |
| JP | 2004-532878 | 10/2004 |
| JP | 2005-053846 | 3/2005 |
| JP | 2006-506351 | 2/2006 |
| JP | 2008-050312 | 3/2008 |
| JP | 2018-512063 | 5/2018 |
| JP | 2018-512064 | 5/2018 |
| KR | 10-2004-0029996 | 4/2004 |
| KR | 10-2005-0049489 | 5/2005 |
| KR | 10-2015-0028297 | 3/2015 |
| WO | WO-2010/073946 | 1/2010 |
| WO | WO-2013/186462 | 12/2013 |
| WO | WO-2016/153893 | 9/2016 |
| WO | WO-2016/160347 | 10/2016 |

OTHER PUBLICATIONS

Roy et al. Spectrochimica Acta Part A 73, 201-204 (Year: 2009).*
Ribeiro, et al.; Chemical stability study of vitamins thiamine, riboflavin, pyridoxine and ascorbic acid in parenteral nutrition for neonatal use; Nutrition Journal; Biomed Central; vol. 10; No. 1; pp. 1-9; May 2011.
Supplementary European Search Report; EP16769359; Completion Date: Aug. 8, 2018; dated Aug. 22, 2018.
Supplementary European Search Report; EP16769365; Completion Date: Aug. 28, 2018; dated Sep. 4, 2018.
Supplementary European Search Report; EP16773728; Completion Date: Sep. 11, 2018; dated Oct. 1, 2018.
Zipfel, et al.; Live tissue intrinsic emission microscopy using multiphoton-excited native fluorescence and second harmonic generation; PNAS; vol. 100; No. 12; pp. 7075-7080; Jun. 2003.

* cited by examiner

*– Significant from baseline*
Mean L* values of undereye (a), cheek (b), and contrast (c) for Stick product format.

*– Significant from baseline*
Mean L* values of undereye (a), cheek (b), and contrast (c) for Cream product format.

Comparison of L* values between the Stick and the Cream on the undereye (a), cheek (b), and contrast (c).

\* - *Significant from baseline*

Mean a\* values of undereye (a) and cheek (b) for Stick product format.

\* - *Significant from baseline*

Mean a\* values of undereye (a) and cheek (b)) for the Cream product format.

Comparison of a\* values between the Stick and the Cream on the undereye (a) and cheek (b).

*- Significant from baseline
Mean b\* values of undereye (a) and cheek (b) for the Stick product format.

\* - *Significant from baseline*

Mean b\* values of undereye (a), cheek (b) for Cream product format.

\* - *Stick format Significant from cream format*
Comparison of b\* values between the Stick and the Cream on the undereye (a), cheek (b)

METHOD OF STABILIZING RIBOFLAVIN

BACKGROUND OF THE INVENTION

Field of the Invention

The present invention relates to optically-activated systems and cosmetic and/or dermatological compositions thereof. More particularly, the optically-activated systems absorb ambient light and re-emit visible light to reduce the visual perception of skin imperfections including, dark under eye circles, hyperpigmentation, rosacea, lines, wrinkles, enlarged pores, cellulite, uneven skin tone, and the like. The optically-activated systems may take the form of lotions, creams, gels, mousses, sticks, powders, and so forth, and may be used in various cosmetic or dermatological preparations, for example, make-up foundations and concealers, and skin treatment products, such as moisturizers.

Description of the Prior Art

A wide variety of personal care compositions has been developed to improve skin appearance; that is, to reduce the appearance of wrinkles, fine lines, enlarged pores, and so forth, to achieve natural, translucent, more even-toned and youthful appearing skin. Such compositions have traditionally utilized light subtraction materials (pigments), fluorescent brighteners, soft focus technology, and/or biologically active anti-aging ingredients.

Reducing the appearance of dark under eye circles in particular has proved a particularly difficult challenge in the cosmetic and dermatological industries. Typical make-ups and concealers do not provide a natural appearance to the skin under the eyes, but only mask the appearance of skin imperfections. For example, current products on the market for targeting dark under eye circles (often referred to as DUEC) contain one or more of metal oxide pigments, dyes and/or lakes, mica, peptides, and botanicals.

The use of a combination of light scattering with fluorescent light emission to camouflage skin imperfections is known from U.S. Pat. No. 7,306,809 which discloses optically-activated particles for use in cosmetic compositions. The optically-activated particles comprise a solid nylon substrate having a synthetic fluorescent compound trapped therein. The fluorescent compound-treated substrate is coated with cross-linked polyvinyl alcohol (PVA). The optically-activated particles emit and diffuse visible blue light which is said to illuminate shadows in skin and/or camouflage fine lines, creating the illusion that such imperfections do not exist. Nevertheless, treatment of DUEC remains a challenge. Most desired by consumers are natural looking compositions which do not mask the skin but which nevertheless reduce the visual perception of skin imperfections, and dark under eye circles, in particular.

Accordingly, there remains a need in the art for improved cosmetic and dermatological systems which are capable of obscuring discolorations and uneven surface texture by imparting a perception of natural, smooth and even-toned skin to observers. The systems of the present invention meet this need by harnessing ambient light and concentrating the increased light reflection in the area of the skin imperfection, and in particular, under the eye.

SUMMARY OF THE INVENTION

The present invention is directed to novel optically-activated systems used alone or in topically applied cosmetic and/or dermatological compositions, and methods of making the optically-activated systems. The topically applied optically-activated systems reduce the visual perception of skin imperfections. More particularly, the present invention is directed to optically-activated systems comprising a complex of a fluorescent compound and a substrate for the fluorescent compound. The fluorescent compound absorbs ambient (ultraviolet to visible) light and re-emits light of longer wavelength in the visible region in the range of from about 300 nm to about 750 nm.

The optically-activated systems, when applied to skin, absorb ambient light and re-emit visible light to reduce the appearance of skin imperfections including dark under eye circles, hyperpigmentation, rosacea, and similar discolorations. The optically-activated systems also provide an illuminating radiant effect on aging skin which serves to minimize the appearance of lines, wrinkles, enlarged pores, cellulite, and the like, as a result of the increased light emission in the affected areas.

The optically-activated systems may be used in the preparation of topically applied products which may take the form of, for example, gels, emulsions (e.g., lotions, creams), serums, mousses, sticks, powders, and so forth. Such products may include, but are not limited to, a make-up foundation, a concealer, a blusher, an eye shadow, or a skin treatment product, such as a moisturizer, a sunscreen, or an anti-wrinkle product.

According to one aspect of the present invention, novel, optically-activated systems comprising, consisting of, or consisting essentially of, a complex of at least one fluorescent compound and at least one substrate for the at least one fluorescent compound are provided. The substrate may be any material to which the fluorescent compound is capable of semi-permanently or permanently adhering or affixing thereto, by one or more of hydrogen bonding, Van der Waals forces, covalent bonding, or a combination thereof. For example, the substrate may have functional groups, such as, but not limited to, —OH, —NH$_2$, —C(O)O—, isohydrocyanate, hydrazine, thiol, or a combination of any two or more thereof. The fluorescent compound is activated by absorption of light in the ultraviolet (UV) to visible region of the electromagnetic spectrum and re-emits visible light of longer wavelength. In a preferred embodiment of the present invention, the re-emitted light is in the blue-green-yellow region of the electromagnetic spectrum.

By use of the term "consisting essentially of", it is intended that the optically-activated systems and methods of the present invention contain no further component or step which would materially and adversely affect the basic and novel characteristics of the claimed systems, the basic and novel characteristics of the optically-activated systems being the capability of the optically-activated systems to absorb ambient light and re-emit light in the visible range to reduce the visual appearance of skin imperfections when the system is applied to skin having the imperfections.

According to one embodiment of this aspect of the present invention, the optically-activated system may be a cosmetic composition useful for improving the appearance of at least one skin imperfection, for example, dark under eye circles, hyperpigmentation, rosacea, and other skin discolorations. The optically-activated system may also be a cosmetic composition which provides an illuminating radiant effect on aging skin to improve the appearance of lines, wrinkles, enlarged pores and cellulite as a result of the increased light emission in the affected area(s). Such compositions include the optically-activated complex and a cosmetically acceptable vehicle.

According to another embodiment of this aspect of the present invention, a cosmetic method for improving the appearance of at least one skin imperfection, for example, dark under eye circles, hyperpigmentation, rosacea, lines, wrinkles, enlarged pores and cellulite, is provided. The cosmetic method comprises topically applying the cosmetic composition to skin in need of such treatment and retaining the composition in contact with the skin to improve the appearance of the at least one skin imperfection.

A further aspect of the present invention is concerned with methods of making the optically-activated systems. The methods include affixing at least one fluorescent compound to at least one substrate for the at least one fluorescent compound by covalent bonding, hydrogen bonding, Van der Waals forces or a combination thereof. When activated by absorption of light in the UV to visible range of the electromagnetic spectrum, the at least one fluorescent compound in the complex re-emits light of longer wavelength. The fluorescent compound selected for preparation of the complex, and therefore the wavelength of the re-emitted light, will depend on the ultimate use of the optically-activated system; that is, the skin imperfection the system is intended to address.

In one embodiment of this aspect of the invention, the method of making the optically-activated system comprises (a) mixing at least one substrate for the at least one fluorescent compound with a solution of the at least one fluorescent compound and (b) evaporating liquid to form a complex in the form of a gel. The method may further include the steps of (c) mixing the gel complex thus-produced with a particulate substrate for a time sufficient to permit the gel to be absorbed into pores of the particulate substrate, and thereafter, (d) removing nonabsorbed liquid to result in a powder. Further optional steps include (e) mixing the powder thus-produced with additional gel complex, and (f) removing nonabsorbed liquid, wherein steps (e) and (f) may be repeated at least one more time, for example, steps (e) and (f) may be repeated until all of the pores of the powder are filled. As used herein, with reference to the optically-activated complex, the term "gel" refers to a material having a watery or syrupy consistency rather than a solid or semi-solid form.

In a further embodiment of this aspect of the invention, the at least one substrate is in particulate form, and the method of making the optically-activated system comprises (a) mixing the at least one particulate substrate with a solution of the at least one fluorescent compound for a time sufficient to permit the solution of the at least one fluorescent compound to be absorbed into pores of the at least one particulate substrate; and (b) heating the at least one particulate substrate having the solution of the at least one fluorescent compound absorbed into the pores thereof under vacuum to remove nonabsorbed liquid and to entrap the at least one fluorescent compound in the pores. The method may further comprise the steps of (c) mixing the at least one particulate substrate having the at least one fluorescent compound entrapped in the pores thereof with additional solution of the at least one fluorescent compound for a time sufficient to permit the additional solution of the at least one fluorescent compound to be absorbed into pores of the at least one particulate substrate, and thereafter (d) removing nonabsorbed liquid. Steps (c) and (d) may be repeated at least one time; for example, the steps may be repeated until all pores of the at least one particulate substrate are filled.

Yet a further aspect of the present invention concerns a method of stabilizing riboflavin. The method comprises affixing the riboflavin to at least one substrate for the riboflavin by covalent bonding, hydrogen bonding, Van der Waals forces, or a combination thereof, to form an optically-activated complex, wherein when activated by absorption of light in the UV to visible region of the electromagnetic spectrum the riboflavin in the complex re-emits visible light of longer wavelength in the blue-green-yellow region of the electromagnetic spectrum.

In one embodiment of this aspect of the invention, the method comprises (a) mixing the at least one substrate with a solution of the riboflavin and (b) evaporating liquid to form a gel complex. The method may further include the steps of (c) mixing the gel complex thus-produced with at least one particulate substrate for a time sufficient to permit the gel complex to be absorbed into pores of the at least one particulate substrate, and thereafter, (d) removing nonabsorbed liquid to result in a powder. The method may further include the following steps (e) mixing the powder thus-produced with additional gel complex for a time sufficient to permit the gel complex to be absorbed into pores of the powder, and (f) removing nonabsorbed liquid. Steps (e) and (f) may be repeated at least one time; for example, until all pores of the powder are filled.

These and other novel aspects and features of the present invention will become apparent from the following detailed description of the preferred embodiments with reference to the accompanying drawings.

DETAILED DESCRIPTION OF THE PREFERRED EMBODIMENTS OF THE INVENTION

Figure 1:
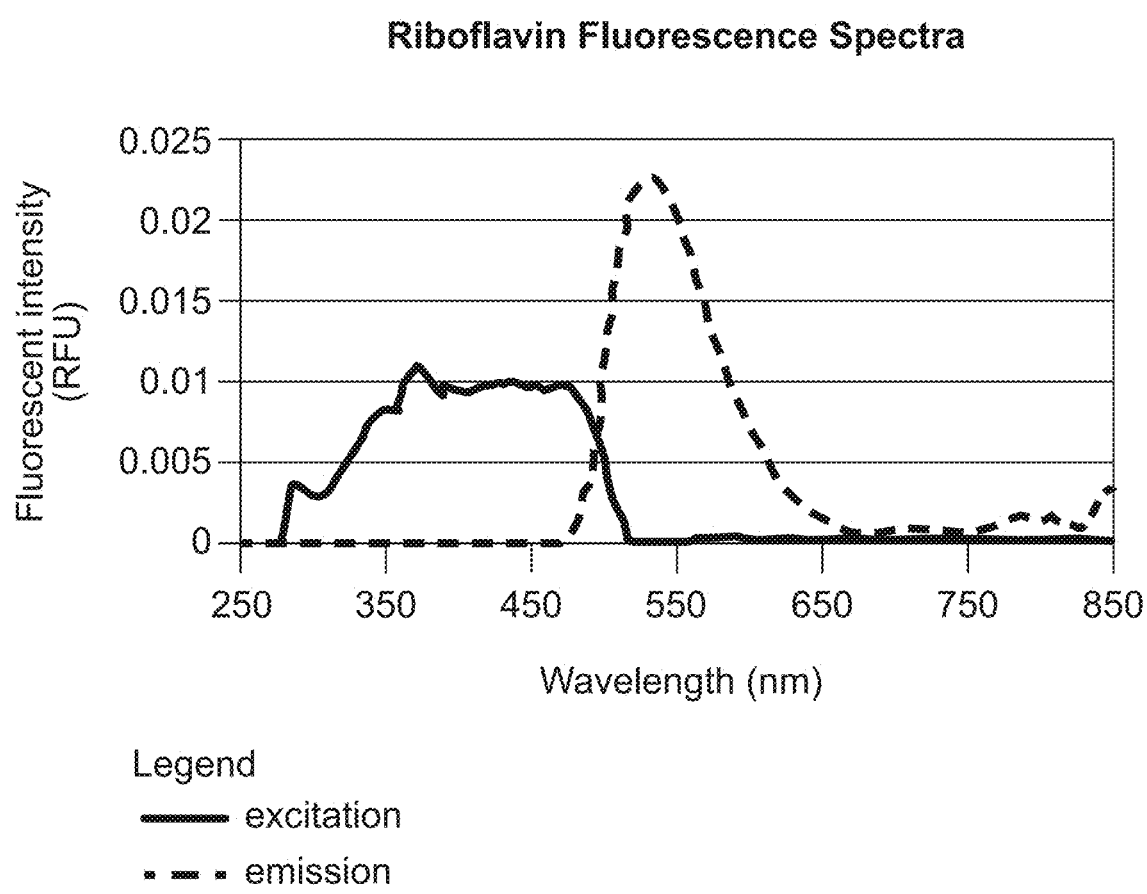
FIG. 1 is a graph showing the absorption and emission spectra for riboflavin.

Novel optically-activated systems according to the present invention comprise, consist of or consist essentially of a complex of at least one natural or synthetic fluorescent compound and at least one substrate for the at least one fluorescent compound. The optically-activated systems absorb ambient light and re-emit and/or reflect visible light to improve the visual perception of skin imperfections.

In the present invention, "optically-activated" means that electrons in the fluorescent compound in the systems of the present invention are excited by the absorption of light in the UV to visible light region of the electromagnetic spectrum. Subsequently, the electrons return to their ground state by re-emitting photons of light of longer wavelength (fluorescing) in the human visible light region with peak emissions in the range of from about 325 nm to about 650 nm. Fluorescing compounds (i.e., fluorophors) which are particularly useful in the systems and methods of the present invention re-emit light in the blue-green-yellow range of the electromagnetic spectrum. Such compounds may be of the natural or synthetic sorts. Natural compounds include, but are not limited to, organic compounds, such as riboflavin, coumarins, pyrenes, quinines, chlorophyll, green fluorescent protein (GFP), and pigments, including opal, autunite, willemite, aragonite, calcite, chabazite, quartz, uranospinite, Znucalite, meta-ankoleite, metalodevite, ALN-GP4 (United Minerals). Examples of useful synthetic compounds include non-protein organic fluorophors which include, but are not limited to, xanthene derivatives, such as fluorescein and rhodamine; coumarin derivatives, for example, 102, 151, 152, 307 and 343; pyrene derivatives; cyanine derivatives; naphthalene derivatives, such as Dansylamide, Acrylodan, Badan and ANTS; Hoechst dyes, including 33258 and 33342; calcium indicators, such as bis-Fura2, Fura 2 AM, Indo 1 AM; magnesium indicators, such as Mag-Fura 2 AM, Mag-Indo 1, Mag-Fura 5; imidazole-based fluorophors, optical brighteners, such as leucophors, and so forth. Preferred examples of fluorescent compounds useful in the present invention are riboflavin, chlorophyll, coumarin, leucophor and quinine. Preferably, the fluorescent compound re-emits light in the blue-green-yellow region of the electromagnetic spectrum.

Peak emission ranges for some exemplary fluorescent compounds are shown in Table 1 below.

TABLE 1

| Fluorophor | Peak emission Range (nm) |
| --- | --- |
| Riboflavin | 510-630 |
| Tinopal | 370-510 |

TABLE 1-continued

| Fluorophor | Peak emission Range (nm) |
| --- | --- |
| Leucophor | 390-500 |
| Quinine | 330-510 |
| Resveratrol | 390-500 |
| Salicylic acid | 350-450 |
| Chlorophyll | 510-600 |

The substrate for the fluorescent compound may be any material having a functional group which is capable of adhering or affixing to, semi-permanently or permanently, the fluorescent compound, by hydrogen bonding, Van der Waals forces, or a combination thereof. The substrate may be a natural or synthetic compound. Natural substrates may have functional groups including, but not limited to, —OH, —NH$_2$, —C(O)O—, isohydrocyanate, hydrazine, thiol, and combinations of any two or more thereof. The substrate may be a polymer such as a polysaccharide selected from the group consisting of cellulose and cellulose derivatives, such as methylcellulose; starch; glycosaminoglycans, for example, hyaluronic acid (HA); glycogen; pectin; chitin, natural gelatins, such as agar; and the like. Synthetic substrates may include, for example, polyacrylic acids or salts of polyacrylic acids, such as sodium (meth) acrylates, for example, Carbopol®, polymethylmethacrylate (PMMA), or poly(2-hydroxyethyl (meth)acrylates ("pHEMA"); a polyamide, such as nylon; isoprene derivatives, such as isoprene maleate polyethylene glycol (PEG); polyvinyl chloride (PVC); polyvinyl dichloride (PVDC); silicone polymers; polyesters; and polyurethanes.

In some embodiments of the invention, the complex of the at least one fluorescent compound and the at least one substrate for the at least one fluorescent compound takes the form of a gel. The substrate in this case is preferably a polysaccharide, as described hereinabove. Exemplary optically-activated complexes of this type include, but are not limited to, riboflavin and HA; chlorophyll and HA; leucophor and HA; quinine and HA; coumarin and HA; riboflavin and methylcellulose; chlorophyll and methylcellulose; leucophor and methylcellulose; quinine and methylcellulose; and coumarin and methylcellulose.

In other embodiments of the invention, the fluorescent compound is entrapped in pores of a particulate substrate. Such synthetic substrates are described hereinabove. Exemplary optically-activated complexes of this type include, but are not limited to, riboflavin and nylon; riboflavin and PMMA; chlorophyll and nylon; chlorophyll and PMMA; leucophor and nylon; leucophor and PMMA; quinine and nylon; quinine and PMMA; coumarin and nylon; and coumarin and PMMA.

In other embodiments of the invention, the optically-activated gel may be further entrapped in the pores of a particulate substrate. Exemplary optically-activated complexes of this type may include, but are not limited to, riboflavin, HA and nylon; riboflavin, HA and PMMA; riboflavin, methylcellulose and nylon, riboflavin, methylcellulose and PMMA, chlorophyll, HA and nylon; chlorophyll, HA and PMMA; leucophor, HA and nylon; leucophor, HA and PMMA; quinine, HA and nylon; quinine, HA and PMMA; coumarin, HA and nylon; and coumarin, HA and PMMA.

It would be understood by those skilled in the art that the optically-activated complex of the present invention may include one or more fluorescent compounds and one or more substrates for the fluorescent compound(s). Additionally, the systems of the present invention may include additional fluorescent compounds which do not form a part of the complex. The systems may also include additional compounds which are not affixed to the complex, but which are of the type which may serve as substrates in a complex, such as an optical brightener, for example leucophor.

Riboflavin (Vitamin $B_2$), the general structure of which is shown below, is a preferred fluorescent material for use in the systems of the present invention. The fluorescent spectrum of riboflavin is shown in FIG. 1 in which fluorescence absorption and emission are measured in RFUs (relative fluorescence units). Riboflavin absorbs light in the visible/near UV region of the electromagnetic spectrum, from about 260 nm to about 460 nm, and re-emits light in the visible region between about 470 nm and about 650 nm, with a peak at about 530 nm.

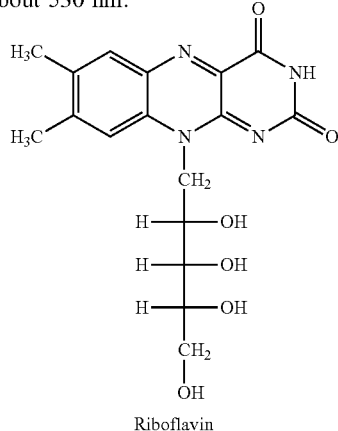

Riboflavin

Figure 2:
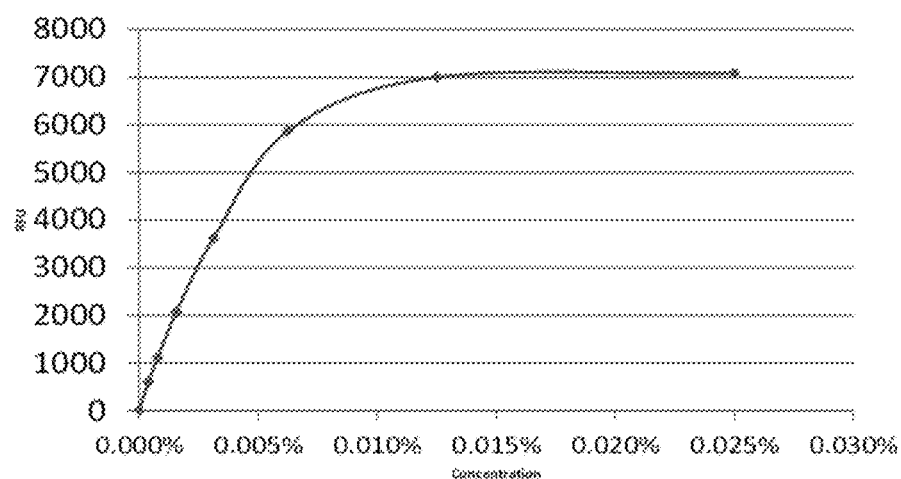
FIG. 2 is a graph showing the concentration-dependent fluorescence of riboflavin.

FIG. 2 demonstrates that the fluorescence of riboflavin is concentration-dependent. As measured using a spectrofluorometer (e.g., a SpectraMax™ Gemini EM Dual-Scanning Microplate Spectrofluorometer), UV light at 320 nm, the minimum wavelength absorbed by riboflavin, resulted in a major peak of fluorescence emitted by riboflavin in water of 538 nm.

Riboflavin is stable to heat, acid and oxidation. However, it is sensitive to light, particularly, UV light, as in sunlight. When riboflavin is irradiated, it degrades into the compound lumichrome and fragments.

Riboflavin is available as a brownish particulate material, but when it is dissolved in water, at neutral pH, the result is a yellowish green solution which displays yellowish green fluorescence due to electrolytic dissociation (e.g., dissociation of hydrogens, principally the primary alcohol hydrogens) and the emission/reflection of photons of light. When the water is removed from the solution, however, there can be no dissociation and no fluorescence is observed. Therefore, once a topical aqueous-containing composition comprising riboflavin is applied to the skin, and the water evaporates, fluorescence ceases to occur.

Surprisingly, the inventors discovered that when riboflavin is combined with hyaluronic acid in solution, the viscosity of the solution increases and a gel is formed. No loss of fluorescent activity is observed when water is removed. Hyaluronic acid, the general structure for which is shown below, possesses a high hydrogen bonding capability.

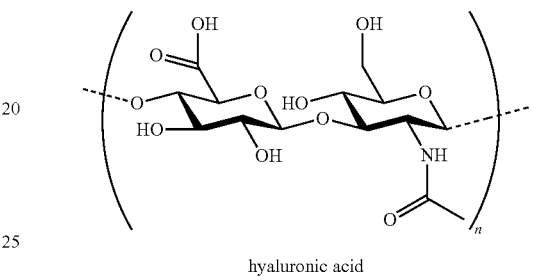

hyaluronic acid

While not wishing to be bound by any particular model, the inventors theorize that, in an aqueous medium, the hydrogens (i.e., mostly the primary alcohol hydrogens) of riboflavin dissociate, and that, as shown by structure (I) below, covalent (ester) bonds form between the riboflavin and the hyaluronic acid forming a riboflavin-hyaluronic acid complex. Alternatively, it is theorized that the riboflavin-hyaluronic acid complexes may be formed by hydrogen bonding, as shown in structure (II) below, Van der Waals forces, or a combination thereof. Additionally, it is theorized that covalent bonding, hydrogen bonding and bonding via Van der Waals forces may occur in the same complex, as shown in structure (III) below. In any case, these complexes remain fixed throughout their manufacture, storage and use. General structures demonstrating these linkages are shown below.

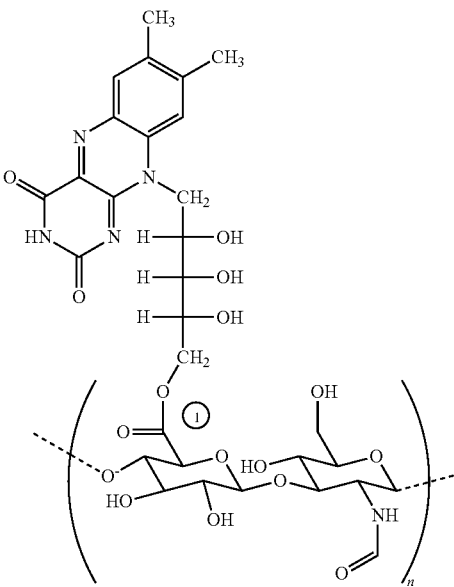

(I)

-continued

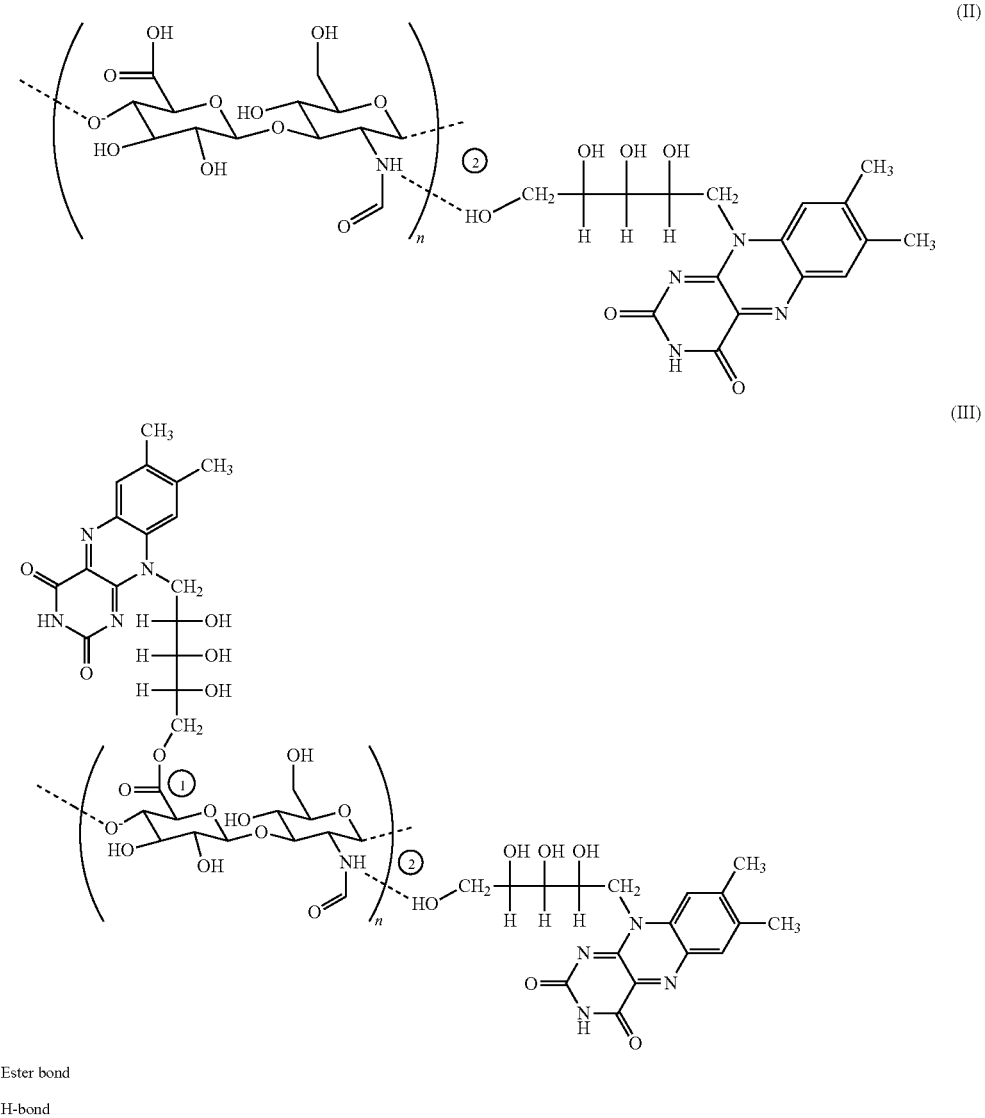

① Ester bond
② H-bond

Optically-activated systems of the present invention, whether the complexes are used alone, or as part of cosmetic and/or dermatological compositions together with a cosmetically and/or dermatologically acceptable vehicle, and applied to skin before or during activation by ambient light (e.g., sunlight), continue to fluoresce in the presence of the activating ambient light until the product is washed away. The systems of the present invention are continually activated by absorption of light in the UV to visible region of the electromagnetic spectrum. The riboflavin-containing systems thus-produced stabilize the riboflavin against degradation from exposure to light, and also against dissociation in aqueous media. Cosmetic compositions containing a complex of at least one fluorescent compound and at least one substrate for the fluorescent compound are suitable for use in methods for improving the appearance of at least one skin imperfection selected from the group consisting of dark under eye circles, hyperpigmentation, rosacea, lines, wrinkles, enlarged pores and cellulite.

The at least one fluorescent compound may be present in the optically-activated systems of the present invention in amounts in the range of from about 0.001% to about 2% by total weight of the system including any amounts therebetween. For example, the at least one fluorescent compound may be present in the systems of the invention in amounts in the range of from about 0.01% to about 0.2%.

The at least one substrate may be present in the optically-activated systems of the present invention in amounts in the range of from about 0.05% to about 25% by total weight of the system, including any amounts therebetween. For example, the at least one substrate may be present in the systems in amounts in the range of from about 0.5% to about 15% by total weight of the system.

The optically-activated system of the present invention may consist of the complex of the at least one fluorescent compound and the at least one substrate for the at least one fluorescent compound, preservative and water, which may be applied alone to skin, for example, in the form of a gel. The complex may comprise in the range of from about 0.01% to about 2.0% of the at least one fluorescent compound, from about 0.5% to about 15% of the substrate and about 80% water. In accordance with one preferred embodiment of the invention, the complex may comprise about 0.1% of the fluorescent compound, about 8% of the substrate and about 80% water, by total weight of the complex.

In some preferred embodiments of the invention, the complex containing the fluorescent compound, the substrate for the fluorescent compound, preservative and water, may be combined with other ingredients in a cosmetic or dermatological composition. In such a system, the complex may take the form of a gel or may be dried and ground to a powder which is then incorporated into the cosmetic or dermatological composition. The complex may be present in the composition in amounts in the range of from about 0.1% to about 20% by total weight of the system. For example, the complex may be present in the compositions of the present invention in amounts in the range of from about 0.5% to about 15% by total weight of the composition.

The optically-activated systems of the present invention may therefore take the forms of topically applicable cosmetic compositions, including treatment products, such as moisturizers, and color cosmetics, such as concealers, to reduce the appearance of skin discolorations, for example, dark under eye circles. The optically-activated systems may also take the form of make-up foundations, pressed powders, concealers, blushers, eye shadows, and the like, to reduce the appearance of skin discolorations, for example, hyperpigmentation, and the redness due to rosacea, as well as to reduce the appearance of skin imperfections particularly associated with aging skin, including lines, wrinkles, enlarged pores, cellulite and the like. The "light release technology" of the optically-activated systems of the present invention reduces the visual perception of skin imperfections by increasing the visible light emission in the area of the skin to which the composition is applied.

The inventors further discovered that optically-activated systems of the present invention, when further combined with one or more additional materials, which reflect blue-green-yellow light (e.g., from about 450-590 nm) possess increased energy intensity which is demonstrated by enhanced fluorescent activity. Therefore, in preferred embodiments of the present invention, cosmetic and/or dermatological compositions comprising the novel optically-activated complexes in a topically acceptable cosmetic and/or dermatological carrier include at least one optically reflective material, for example, an iridescent/pearlescent or light scattering material, to boost or enhance the effects imparted to the compositions by the optically-activated complexes. Such ingredients absorb ambient light, and then release the light, backscattering and/or reflecting visible light back to an observer. "Backscattering" is the reflection of light waves back to the direction from which they came—a diffuse reflection rather than a spectral reflection like a mirror in which light from a single incoming direction is reflected into a single outgoing direction, the angle of incidence equaling the angle of reflection.

Mica-, glass-, and plastics-based substances are examples of materials which have been observed to demonstrate reflective, iridescent, pearlescent and/or light-scattering effects. Iridescence is an optical phenomenon of surfaces in which hue changes in correspondence with the angle from which the surface is viewed, or the angle of illumination changes. Iridescence is often the result of multiple reflections from multiple surfaces in which phase shift and interference of the reflections modulate the incidental light. One example of such a material which is useful in the systems of the present invention is KTZ® Interval Green (Kobo), which has a green reflection color. This material, based on a mica substrate coated with titanium dioxide and tin oxide, has a particle size of from about 10 to about 60 µm, and creates a pearlescent effect, interference colors, angle-related color travel and coverage. Light re-emitted from the optically-activated fluorescent compound-containing complexes of the present invention hits the titanium dioxide-coated mica particles which in turn act like tiny mirrors to reflect and backscatter the light. This effect continues indefinitely in the presence of an optically-activating light source (e.g. UV light). A further example of a light-scattering material useful in the systems of the present invention is a luminescent powder comprising silica beads coated with clear polyurethane and green dye, available as Chrono-Sphere® Opticals Brite, available from Alzo/Arch. The clear coating changes the angle in which light enters the beads. As a result, the focal point is shifted form the outer edge of the silica bead into the center thus distorting the image captured by a viewer. The modified image obscures imperfections in the skin, such as lines and wrinkles, without being opacifying, and further decreases skin redness. Green light re-emitted from the optically-activated complexes in the systems of the present invention passes through the glass beads and an intensified green light emerges.

Other reflective materials useful in the systems of the present invention include titanium dioxide-coated mica, available as Flamenco blue from BASF Chemical Co., an iridescent material transmit green light, which are useful in the systems of the present invention include, but are not limited to, KTZ® Interfine Green, KTZ® Shimmer Green, Timiron® Splendid Green, Ronastar® Aqua Sparks and Ronastar® Green Sparks interference pigments.

The optically-activated systems of the present invention may include soft focus materials. Such materials may include glass beads and plastic beads, such as those formed of Polyhydroxyethyl methacrylate (pHEMA) and copolymers thereof or Poly (methyl) methacrylate (PMMA). PMMA is available as Ganzpearl-GM-0600W from Ganz Chemical Co. Ltd. PMMA is a lightweight, transparent thermoplastic material, often used as a substitute for glass in many applications, which transmits up to 92% of visible light and gives a reflection of about 4% from each of its surfaces. As described hereinabove, PMMA and pHEMA may serve as substrates when affixed to fluorescent compounds in the optically-activated complexes of the present invention.

In particularly preferred embodiments of the present invention the optically-activated systems include reflecting, backscattering and soft focus materials.

The systems of the present invention may also include other natural ingredients which absorb UV light and re-emit visible light of longer wavelengths. One example is extract of *Verbascum Thapsus* flower, available as Luminescine® from TRI-K, which absorbs UV light (at about 420 nm) and re-emits light with the most significant emission in the 470-600 nm range (e.g., blue-green-yellow region) of the electromagnetic spectrum.

Further examples of reflective materials which may be used in the systems of the present invention include pearls, glass flakes, glass fibers, titanium oxides, iron oxides, tin oxide, chromium oxide, barium sulfate, $MgF_2$, $CeF_3$, ZnS, ZnSe, $SiO2$, $Al_2O_3$, MgO, $Y_2O_3$, $SeO_3$, SiO, $HfO_2$, $ZrO_2$, $CeO_2$, $Nb_2O_5$, $Ta_2O_5$ and $MoS_2$, $Al/SiO_2/Al/SiO_2/Al$, $Cr/MgF_2/Al/MgF_2/Cr$; $MoS_2/SiO_2/Al/SiO_2/MoS_2$; $Fe_2O_3/SiO_2/Al/SiO_2/Fe_2O_3$; $Fe_2O_3/SiO_2/Fe_2O_3/SiO_2/Fe_2O_3$; $MoS_2/SiO_2/mica$-oxide/$SiO_2/MoS_2$; $Fe_2O_3/SiO_2/mica$-oxide/$SiO_2/Fe_2O_3$, $TiO_2/SiO_2/TiO_2$; $TiO_2/Al_2O_3/TiO_2$, $SnO/TiO_2/SiO_2/TiO_2/SnO$, $Fe_2O_3/SiO_2/Fe_2O_3$ and $SnO/Mica/TiO_2/SiO_2/TiO_2/Mica/SnO$. $MoS_2/SiO_2/Al/SiO_2/MoS_2$;

$Fe_2O_3/SiO_2/Al/SiO_2/Fe_2O_3$ and $Fe_2O_3/SiO_2/Fe_2O_3/SiO_2/Fe_2O_3$; $SnO/TiO_2/SiO_2/TiO_2/SnO$, $Fe_2O_3/SiO_2/Fe_2O_3$ and $SnO/Mica/TiO_2/SiO_2/TiO_2/Mica/SnO$, goniochromatic fibers, $MgF_2$, $CeF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$ and $MoS_2$, and mixtures thereof. $Al/SiO_2/Al/SiO_2/Al$; $Cr/MgF_2/Al/MgF_2/Cr$; $MoS_2/SiO_2/Al/SiO_2/MoS_2$; $Fe_2O_3/SiO_2/Al/SiO_2/Fe_2O_3$; $Fe_2O_3/SiO_2/Fe_2O_3/SiO_2/Fe_2O_3$; $MoS_2/SiO_2/mica$-oxide$/SiO_2/MoS_2$; $Fe_2O_3/SiO_2/mica$-oxide$/SiO_2/Fe_2O_3$, $TiO_2/SiO_2/TiO_2$; $TiO_2/Al_2O_3/TiO_2$, $SnO/TiO_2/SiO_2/TiO_2/SnO$, $Fe_2O_3/SiO_2/Fe_2O_3$ and $SnO/Mica/TiO_2/SiO_2/TiO_2/Mica/SnO$. The metal may be chosen, for example, from Ag, Au, Cu, Al, Ni, Sn, Mg, Cr, Mo, Ti, Pt, Va, Rb, W, Zn, Ge, Te, Se and alloys thereof. Ag, Au, Al, Zn, Ni, Mo, Cr, Cu and alloys thereof (for example bronzes and brasses) are preferred metals, Particles of glass coated with a metallic layer, $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$ and mixtures or alloys thereof, silicone resins. Reflective particles comprising a stack of at least two layers of polymers are sold by 3M under the name Mirror Glitter. These particles comprise layers of 2,6-PEN and of polymethyl methacrylate in an 80/20 mass ratio. Such particles are described in U.S. Pat. No. 5,825,643. $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, and alloys, polymers and combinations thereof. Examples of symmetrical multilayer interference structures that may be used in the systems prepared in accordance with the invention include, for example, $Al/SiO_2/Al/SiO2/Al$, available from Dupont de Nemours; $Cr/MgF_2/Al/MgF_2/Cr$, sold under the name Chromaflair® and available from Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, sold under the name Sicopearl® by BASF; $MoS_2/SiO_2/$mica-oxide$/SiO_2/MoS_2$; $Fe_2O_3/SiO_2/$mica-oxide$/SiO_2/Fe_2O_3$; $TiO_2/SiO_2/TiO_2$, $TiO_2/Al_2O_3/TO_2$, $SnO/TiO_2/SiO_2/TiO_2/SnO$, $Fe_2O_3/SiO_2/Fe_2O_3$, $SnO/Mica/TiO_2/SiO_2/TiO_2/Mica/SnO$, sold under the name Xirona® by Merck (Darmstadt). As further examples, these pigments may have a silica/titanium-oxide/tin oxide structure sold under the name Xirona® Magic, pigments of silica/brown-iron oxide structure sold under the name Xirona® Indian Summer, or pigments of silica/titanium oxide/mica/tin oxide structure sold under the name Xirona® Carribean Blue, all available from Merck. Mention may also be made of the Infinite Colors pigments, available from Shiseido. Depending on the thickness and the nature of the various layers, different effects are obtained. Thus, with the $Fe_2O_3/SiO_2/Al/SiO_2/Fe_2O_3$ structure, the color changes from green-golden to red-grey for $SiO_2$ layers of 320 to 350 nm; from red to golden for $SiO_2$ layers of 380 to 400 nm; from violet to green for $SiO_2$ layers of 410 to 420 nm; from copper to red for $SiO_2$ layers of 430 to 440 nm.

As dyes that may be used, examples include, but are not limited to, Sudan red, DC Red 17, DC Green 6, P-carotene, soybean oil, Sudan brown, DC Yellow 11, DC Violet 2, DC orange 5, quinoline yellow, annatto, carotenoid derivatives, for instance lycopene, beta-carotene, bixin and capsanthin, and/or mixtures thereof, these dyes being liposoluble. Water-soluble dyes, for example, copper sulfate, iron sulfate, water-soluble sulfopolyesters such as those described in FR-96,154,152, rhodamines, natural dyes (carotene, beetroot juice), methylene blue and caramel, may also be used.

Optical brighteners also may be incorporated into the systems of the present invention in addition to their roles as substrates. Optical brighteners appear brighter than the light that strikes them and may be used to make a surface appear less yellow and more blue-green, thus brightening shadowed or dark areas of the skin. Optical brighteners are virtually colorless dyes that work via a fluorescent mechanism, absorbing light in the UV range (300-400 nm) and re-emitting light in the visible violet to blue to green range. Optical brighteners may be encapsulated in microspheres. Optical brighteners useful in the systems of the present invention include, but are not limited to, triazine-stilbenes (di-, tetra- or hexa-sulfonated); biphenyl-stilbenes coumarins; imidazolines; diazoles; triazoles; benzoxazonlines; derivatives of stilbene and 4,4â€²-diaminostilbene; derivatives of benzene and biphenyl; pyrazolines, derivatives of bis(benzoxazol-2-yl), coumarins, carbostyrils, naphthalimides, s-triazines, and pyridotriazoles, derivatives of stilbene and 4,4â€²-diaminostilbene; derivatives of benzene and biphenyl; pyrazolines, derivatives of bis(benzoxazol-2-yl), coumarins, carbostyrils, naphthalimides, s-triazines, pyridotriazoles, and inorganic fluorescent glasses. Examples of optical brighteners useful in the systems of the present invention include, but are not limited to, Lipolight® OAP/PVA, available from Lipo Chemicals; Leucophor BSB, available from SandozChemicals; and Tinopal®, available from BASF.

The additional reflective and/or light scattering materials, e.g., the iridescent/pearlescent materials, the soft focus materials and/or the optical brighteners, may be present in compositions of the present invention in amounts sufficient to further enhance the diffusion and/or reflection of the light emitted and reflected by the novel riboflavin-hyaluronic complex on skin to which the system is applied. Preferably, such additional reflective materials may be present in the systems in the range of from about 0.01 to about 75% by total weight of the systems, preferably from about 0.1 wt. % to about 25 wt. %, more preferably from about 1 wt. % to about 10 wt. %, such as from about 3 wt. % to about 5 wt. %.

The optical effect of cosmetic systems according to the present invention may therefore be attributable to a combination of diffuse light emission (i.e., fluorescence) and the reflection of the re-emitted visible light, and optionally as well, to back scattering of the re-emitted and reflected light. However, the present invention does not rely solely on those effects. The visible light emitted by the optically-activated systems of the present invention is concentrated in the blue-green-yellow visible region of the electromagnetic spectrum (i.e., about 450 nm to about 600 nm). The human eye has the greatest visual sensitivity to the green portion of the spectrum (at about 555 nm). The inventors have appreciated that the human under eye area, in contrast to the human cheek area, exhibits a reduced luminescence in the blue-green region of the electromagnetic spectrum.

It may be noted that collagen reflects in green wavelengths, and the under eye area typically is lacking in collagen relative to the cheek area. The interaction of HA with CD44 cell surface glycoprotein is a driver of collagen synthesis. The systems of the present invention have been developed to increase the reflection of blue-green-yellow visible light and to reduce the reflection of red light, particularly in the under eye region, so as to reduce the contrast between the under eye area and the cheek areas, and thus to reduce the appearance of discoloration associated with skin imperfections, and in particular, DUEC. It is theorized that the optically-activated systems of the present invention, in addition to their light release technology and increasing greenness of dark under eye circles (DUEC), due to the presence of the fluorescing compound, may also stimulate collagen production which may further contribute in the long-term to the increase in greenness of DUEC. The inventors have also discovered that the compositions of the present invention may be used to reduce the red appearance of rosacea, where, in this instance as well, this area of the skin demonstrates reduces green luminescence compared with skin that is not affected by rosacea. Compositions according to the present invention may be applied to skin areas affected by rosacea to reduce the contrast between the affected and the unaffected regions and thus achieve a more even-toned complexion. In the short term, compositions comprising systems of the present invention help to camouflage the appearance of rosacea, and in the long-term, may stimulate the production of collagen.

Cosmetic of the present inventions may be found in a variety of forms, such as anhydrous compositions, aqueous-based solutions, serums, gels, creams, lotions, mousses, sticks, sprays, ointments, essences, pastes, microcapsules, or color cosmetic compositions such as foundation, blush, eye shadow, and the like. They may contain other additional cosmetically and/or dermatologically acceptable ingredients, such as skin lightening agents, antioxidants, anti-inflammatory agents, botanicals, humectants, moisturizers, emollients, skin conditioning agents, sunscreens, colorants, perfumes, oils, preservatives, surfactants, emulsifiers, thickening agents, DNA repair agents, binders, pigments and pigment dispersion agents, and the like.

In forming compositions according to the invention, the fluorescent compound-substrate complex, being water-soluble, also may be solvated in various polar solvents, typically ingredients referred to as humectants such as glycerine or alkylene glycols, prior to formation of an anhydrous emulsion, or may be dispersed or solubized in the water phase of an emulsion.

In the case where the compositions are in the form of aqueous solutions, dispersions or emulsions, in addition to water the aqueous phase may contain one or more aqueous phase structuring agents, that is, an agent that increases the viscosity or, or thickens, the aqueous phase of the composition. This is particularly desirable when the composition is in the form of a serum or gel. The aqueous phase structuring agent should be compatible with the optically-activated systems, and also compatible with the other ingredients in the formulation. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below. As the optically-activated systems are in water soluble form, an aqueous phase thickening agent also contributes to stabilizing this ingredient in the composition.

Polysaccharides may be suitable aqueous phase thickening agents, in addition to serving as possible substrates in the complexes in systems of the present invention. Examples of such polysaccharides include naturally derived materials such as agar, agarose, alicaligenes polysaccharide, algin, alginic acid, acacia gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

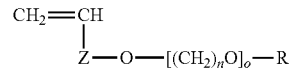

wherein Z is $—(CH_2)_m$, wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of $C_{10-30}$ alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

One particularly suitable type of aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesqui-isostearate; or Aristoflex HMB which is ammonium acryloyldimethyltaurate/beheneth-25 methacrylate crosspolymer, and the like.

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

In the event the compositions of the invention are in emulsion form, the composition will comprise an oil phase. Oily ingredients are desirable for the skin moisturizing and protective properties. Oils, if present, will form a barrier on the skin so that the optically-activated complex present in the composition remains on the skin. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

Suitable volatile oils generally have a viscosity ranging from about 0.5 to 5 centistokes 25° C. and include linear silicones, cyclic silicones, paraffinic hydrocarbons, or mixtures thereof. Volatile oils may be used to promote more rapid drying of the skin care composition after it is applied to skin. Volatile oils are more desirable when the skin care products containing the optically-activated complex are being formulated for consumers that have combination or oily skin. The term "combination" with respect to skin type means skin that is oily in some places on the face (such as the T-zone) and normal in others.

Cyclic silicones are one type of volatile silicone that may be used in the composition. Such silicones have the general formula:

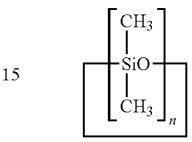

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centi stokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

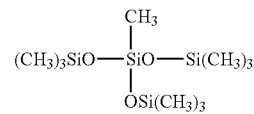

Methyl trimethicone may be purchased from Shin-Etsu Silicones under the tradename TMF-1.5, having a viscosity of 1.5 centistokes at 25° C.

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

Suitable esters are mono-, di-, and triesters. The composition may comprise one or more esters selected from the group, or mixtures thereof.

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, *Camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiososstearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

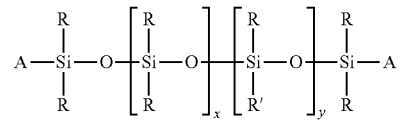

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

Various types of fluorinated oils may also be suitable for use in the compositions including but not limited to fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588 all of which are hereby incorporated by reference, which are commercially available from Montefluos under the trademark Fomblin.

In the case where the composition is anhydrous or in the form of an emulsion, it may be desirable to include one or more oil phase structuring agents in the cosmetic composition. The term "oil phase structuring agent" means an ingredient or combination of ingredients, soluble or dispersible in the oil phase, which will increase the viscosity, or structure, the oil phase. The oil phase structuring agent is compatible with the optically-activated complex, particularly if the optically-activated complex may be solubilized in the nonpolar oils forming the oil phase of the composition. The term "compatible" means that the oil phase structuring agent and optically-activated complex are capable of being formulated into a cosmetic product that is generally stable. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

A variety of oil phase structuring agents may be silicone based, such as silicone elastomers, silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to the following.

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Coming's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossoplymer. Silicone elastomers may also be purchased from Grant Industries under the Gransil trademark.

Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety. It is particularly desirable to incorporate silicone elastomers into the compositions of the invention because they provide excellent "feel" to the composition, are very stable in cosmetic formulations, and relatively inexpensive.

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula wherein:

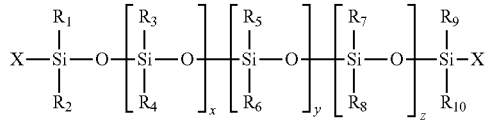

$R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

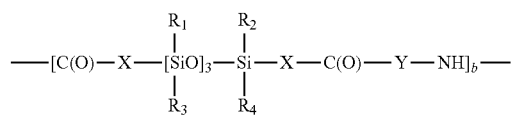

X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

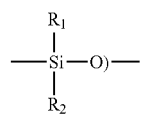

and Y is:
(a) a linear or branched alkylene having from about 1-40 carbon atoms which may be substituted with:
 (i) one or more amide groups having the general formula $R_1CONR_1$, or
 (ii) $C_{5-6}$ cyclic ring, or
 (iii) phenylene which may be substituted with one or more $C_{1-10}$ alkyl groups, or
 (iv) hydroxy, or
 (v) $C_{3-8}$ cycloalkane, or
 (vi) $C_{1-20}$ alkyl which may be substituted with one or more hydroxy groups, or
 (vii) $C_{1-10}$ alkyl amines; or
(b) $TR_5R_6R_7$
 wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

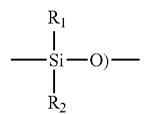

Preferred is where $R_1$, $R_2$, $R_3$, and $R_4$ are $C_{1-10}$, preferably methyl; and X and Y is a linear or branched alkylene. Preferred are silicone polyamides having the general formula:

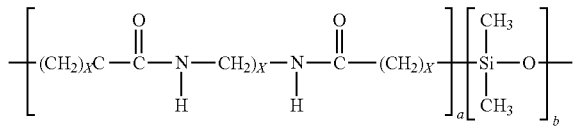

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether. Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

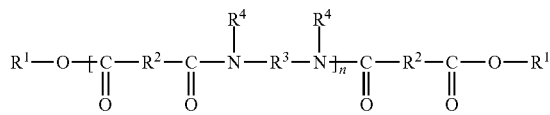

wherein n denotes a number of amide units such that the number of ester groups ranges from about 10% to 50% of the total number of ester and amide groups; each $R^1$ is independently an alkyl or alkenyl group containing at least 4 carbon atoms; each $R^2$ is independently a $C_{4-42}$ hydrocarbon group, with the proviso that at least 50% of the $R^2$ groups are a $C_{30-42}$ hydrocarbon; each $R^3$ is independently an organic group containing at least 2 carbon atoms, hydrogen atoms and optionally one or more oxygen or nitrogen atoms; and each $R^4$ is independently a hydrogen atom, a $C_{1-10}$ alkyl group or a direct bond to $R^3$ or to another $R^4$, such that the nitrogen atom to which $R^3$ and $R^4$ are both attached forms part of a heterocyclic structure defined by $R^4$—N—$R^3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

Also suitable as the oil phase structuring agent may be one or more natural or synthetic waxes such as animal, vegetable, or mineral waxes. Preferably such waxes will have a higher melting point such as from about 50 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

Another type of structuring agent that may be used in the compositions are silicas, silicates, silica silylate, and alkali metal or alkaline earth metal derivatives thereof. These silicas and silicates are generally found in the particulate form and include silica, silica silylate, magnesium aluminum silicate, and the like.

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Suitable silicone surfactants include polyorganosiloxane polymers that have amphiphilic properties, for example contain hydrophilic radicals and lipophilic radicals. These silicone surfactants may be liquids or solids at room temperature.

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

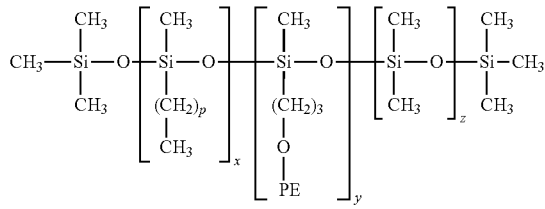

wherein p is 0-40 (the range including all numbers between and subranges such as 2, 3, 4, 13, 14, 15, 16, 17, 18, etc.), and PE is (—$C_2H_4O$)$_a$—(—$C_3H_6O$)$_b$—H wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. Nos. 5,236,986 and 5,412,004, 5,837,793 and 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011. One preferred crosslinked silicone elastomer emulsifier is dimethicone/PEG-10/15 crosspolymer, which provides excellent aesthetics due to its elastomeric backbone, but also surfactancy properties.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula: where RCO is the carboxylic ester radical, X is hydrogen or lower alkyl, and n is the number of polymerized alkoxy groups. In the case of the diesters, the two RCO- groups do not need to be identical. Preferably, R is a C6-30 straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula: wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, *Thermus thermophilis* ferment extract, *Camelina sativa* seed oil, *Boswellia serrata* extract, olive extract, *Aribodopsis thaliana* extract, *Acacia dealbata* extract, *Acer saccharinum* (sugar maple), acidopholus, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, whey protein, and those set forth on pages 1646 through 1660 of the CTFA Cosmetic Ingredient Handbook, Eighth Edition, Volume 2. Further specific examples include, but are not limited to, *Camelia sinensis, Siegesbeckia orientalis, Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officianalis, Citrus medica limonum, Panax ginseng, Siegesbeckia orientalis, Fructus mume, Ascophyllum nodosum, Bifida ferment lysate, Saccharomyces lysate, Glycine soja extract, Beta vulgaris, Haberlea rhodopensis, Polygonum cuspidatum, Citrus aurantium dulcis, Vitis vinifera, Selaginella tamariscina, Humulus lupulus, Citrus reticulata Peel, Punica granatum, Asparagopsis, Curcuma longa, Menyanthes trifoliata, Helianthus annuus, Triticum vulgare, Hordeum vulgare, Cucumis sativus, Evernia prunastri, Evernia furfuracea*, and mixtures thereof.

It may also be desirable to include one or more sunscreens in the compositions of the invention. Such sunscreens include chemical UVA or UVB sunscreens or physical sunscreens in the particulate form. Inclusion of sunscreens in the compositions containing the optically-activated complex will provide additional protection to skin during daylight hours.

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

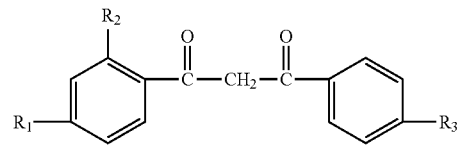

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

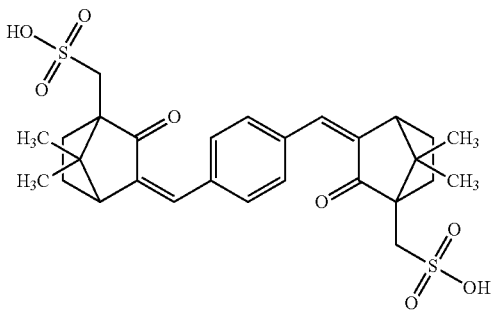 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

UVB sunscreens may also be employed in the systems of the present invention. The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate.

In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

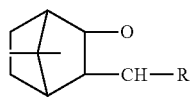

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

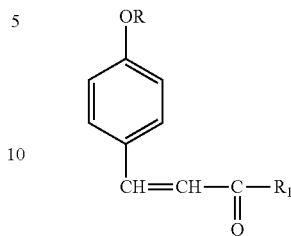

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

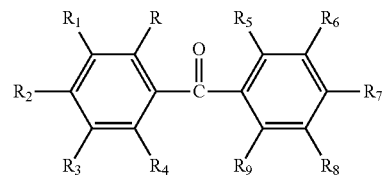

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

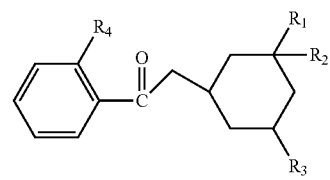

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

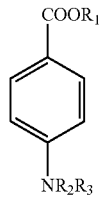

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{18}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-50, preferably about 2-45, most preferably about 5-30. Calculation of SPF values is well known in the art.

The compositions of the invention may contain particulate materials in addition to the optically reflective materials, including other pigments, inert particulates, or mixtures thereof. Suggested ranges for all particulate materials is from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

The particulate matter may be colored or non-colored (for example, white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

The composition may contain 0.001-8%, preferably 0.01-6%, more preferably 0.05-5% by weight of the total composition of preservatives. A variety of preservatives are suitable, including benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, hexylene glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are retinyl palmitate, retinol. retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfate, sodium erythrobate, sodium metabisulfite, sodium sulfite, propyl gallate, cysteine hydrochloride, butylated hydroxytoluene, butylated hydroxyanisole, and so on.

It may also be desirable to incorporate one or more DNA repair enzymes into the systems of the invention. Suggested ranges are from about 0.00001 to about 35%, preferably from about 0.00005 to about 30%, more preferably from about 0.0001 to about 25% of one or more DNA repair enzymes. DNA repair enzymes useful in the compositions of the present invention are those described hereinabove.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI Dermatics under the trade name Roxisomes®, and has the INCI name *Arabidopsis thaliana* extract. It may be present alone or in admixture with lecithin and water. This DNA repair enzyme is known to be effective in repairing 8-oxo-diGuanine base mutation damage.

Another type of DNA repair enzyme that may be used is one that is known to be effective in repairing O6-methyl guanine base mutation damage. It is sold by AGI/Dermatics under the tradename Adasomes®, and has the INCI name Lactobacillus ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of a species of micrococcus), lecithin, and water. Photosomes® comprises a mixture of plankton extract (which is the extract of a biomass which includes enzymes from one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *Bifida* lysate or *Bifida ferment* lysate, the latter a lysate from Bifido bacteria which contains the metabolic products and cytoplasmic fractions when Bifido bacteria are cultured, inactivated and then disintegrated. This material has the INCI name *Bifida ferment* Lysate.

Other suitable DNA repair enzymes include Endonuclease V, which may be produced by the denV gene of the bacteriophage T4. Also suitable are T4 endonuclease; O-6-methylguanine-DNA methyltransferases; photolyases, base glycosylases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; polymerases; ligases; and topoisomerases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as O-6-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch excision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as *Xeroderma pigmentosum* group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-1 or RAD-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog (REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial lysates, biological materials, and the like. For example, botanical extracts may contain DNA repair enzymes.

The invention further comprises methods for treating skin for improvement by applying to the skin in need of the improvement the optically-activated systems of the invention as described hereinabove. The optically-activated systems may be applied in the forms mentioned herein, and may be applied as part of skin care regimens. The optically-activated systems may be applied directly to clean skin in the form of a serum or a day cream. The optically-activated systems may be applied to the skin under or over skin care products. The optically-activated systems may be incorporated into foundations or other color cosmetics. The optically-activated systems of the present invention are activated by absorption of light in the UV to visible region of the electromagnetic spectrum either during or after application to skin. The fluorescent compound in the optically-activated system will continue to fluoresce as long as the system remains in contact with skin and is exposed to and absorbs light in the UV to visible region of the electromagnetic spectrum. The optically-activated systems need only be reapplied in the event the product is washed off, such as after bathing, swimming, excessive perspiring, crying, and so forth.

The present invention is also concerned with methods of making the optically-activated systems. The methods of making an optically-activated system comprising a complex of at least one fluorescent compound and at least one substrate for the fluorescent compound include affixing the at least one fluorescent compound to the at least one substrate for the at least one fluorescent compound by covalent bonding, hydrogen bonding, Van der Waals forces, or a combination thereof. The at least one fluorescent compound in the complex is activated by absorption of light in the UV to visible region of the electromagnetic spectrum and re-emits visible light of longer wavelength in the blue-green-yellow region of the electromagnetic spectrum.

In one embodiment, the step of affixing comprises (a) mixing the at least one substrate with a solution of the at least one fluorescent compound, and (b) evaporating liquid to form the optically-activated complex in the form of a gel. The at least one substrate is preferably a polysaccharide such as a starch; a glycosaminoglycan for example hyaluronic acid; glycogen, pectin, chitin, cellulose and derivatives thereof, such as methylcellulose; a natural gelatin, and combinations thereof.

Optionally, this method includes the further steps of (c) mixing the gel thus-produced with at least one particulate substrate for a time sufficient to permit the gel to be absorbed into pores of the at least one particulate substrate, and thereafter (d) removing nonabsorbed liquid. Optionally, the method further comprises (e) mixing the at least one particulate substrate having the gel incorporated therein with additional gel for a time sufficient to permit the additional gel to be absorbed into pores of the at least one particulate substrate, and (f) removing nonabsorbed liquid, wherein, optionally, steps (e) and (f) are repeated at least one time; for example, steps (e) and (f) may be repeated until all pores of the at least one particulate substrate are filled. Examples of useful particulate substrates include, but are not limited to, a polyamide, a polyacrylic acid or salt thereof, and an isoprene derivative. The polyamide may be nylon; the polyacrylic acid may be poly methyl methacrylate (PMMA) or polyhydroxyethyl methacrylate (pHEMA); and the isoprene derivative may be isoprene maleate polyethylene glycol (PEG).

In accordance with a further method of making the optically-activated systems, the at least one substrate is in the form of particulates, and the method includes the steps of (a) mixing the at least one particulate substrate with a solution of the at least one fluorescent compound for a time sufficient for the solution of the at least one fluorescent compound to be absorbed into pores in the at least one particulate substrate, and (b) heating the at least one particulate substrate having the solution of the at least one fluorescent compound absorbed in the pores thereof under vacuum to remove nonabsorbed liquid and to entrap the at least one fluorescent compound in the pores. Examples of useful particulate substrates include, but are not limited to, a polyamide, a polyacrylic acid or salt thereof, and an isoprene derivative. The polyamide may be nylon; the polyacrylic acid may be poly methyl methacrylate (PMMA) or polyhydroxyethyl methacrylate (pHEMA); and the isoprene derivative may be isoprene maleate polyethylene glycol (PEG).

Optionally, this further method may include the steps of (c) mixing the at least one particulate substrate having the at least one fluorescent compound entrapped in the pores thereof with a further solution of the at least one fluorescent compound for a time sufficient to permit the further solution of the at least one fluorescent compound to be absorbed into pores of the at least one particulate substrate, and thereafter (d) removing nonabsorbed liquid. Steps (c) and (d) may be repeated at least one time, such as, for example, until all pores of the at least one particulate substrate are filled. Examples of useful particulate substrates include, but are not limited to, a polyamide, a polyacrylic acid or salt thereof, and an isoprene derivative. The polyamide may be nylon; the polyacrylic acid may be poly methyl methacrylate (PMMA) or polyhydroxyethyl methacrylate (pHEMA); and the isoprene derivative may be isoprene maleate polyethylene glycol (PEG).

The at least one fluorescent compound may be present in the system in amounts in the range of from about 0.001% to about 2%, by total weight of the system. The at least one substrate for the at least one fluorescent compound may be present in the system in amounts in the range of from about 0.05% to about 25%, by total weight of the system.

The above-described methods may include incorporating one or more additional materials which reflect light in the blue-green-yellow range of the electromagnetic spectrum and enhance the fluorescent activity of the systems. Such materials include optically reflective or light scattering materials, as described hereinabove.

The present invention is further directed to methods of stabilizing riboflavin. These methods include affixing the riboflavin to at least one substrate for the riboflavin by covalent bonding, hydrogen bonding, Van der Waals forces, or a combination thereof, to form an optically-activated complex, wherein when activated by absorption of light in the UV to visible region of the electromagnetic spectrum, the riboflavin in the complex re-emits light of longer wavelength in the blue-green-yellow region of the electromagnetic spectrum.

In accordance with one embodiment of this method, the step of affixing comprises (a) mixing the at least one substrate with a solution of the riboflavin, and (b) evaporating liquid to form the optically-activated complex in the form of a gel. Preferably, the substrate is a polysaccharide such as starch; a glycosaminoglycan, for example, HA; glycogen, pectin, chitin, cellulose and derivatives thereof, such as methylcellulose; a natural gelatin; and combinations thereof.

Optionally, the at least one substrate further comprises a particulate substrate, and the method further comprises (c) mixing the gel thus-produced with at least one particulate substrate for a time sufficient to permit the gel to be absorbed into pores of the at least one particulate substrate, and thereafter (d) removing nonabsorbed liquid. Optionally, the method further comprises (e) mixing the at least one particulate substrate having the gel incorporated therein with additional gel for a time sufficient to permit the additional gel to be absorbed into pores of the at least one particulate substrate, and (f) removing nonabsorbed liquid, wherein, optionally, steps (e) and (f) are repeated at least one time, for example, steps (e) and (f) may be repeated until all pores of the at least one particulate substrate are filled. Examples of the particulate substrate include, but are not limited to, a polyamide, a polyacrylic acid or salt thereof, and an isoprene derivative. The polyamide may be nylon; the polyacrylic acid may be poly methyl methacrylate (PMMA) or polyhydroxyethyl methacrylate (pHEMA); and the isoprene derivative may be isoprene maleate polyethylene glycol (PEG).

In accordance with a further embodiment of the method of stabilizing riboflavin, the at least one substrate is in the form of particulates, and the method comprises (a) mixing the at least one particulate substrate with a solution of the riboflavin for a time sufficient for the solution of riboflavin to be absorbed into pores of the at least one particulate substrate, and (b) heating the at least one particulate substrate having the riboflavin solution absorbed in the pores thereof under vacuum to remove nonabsorbed liquid so as to entrap the riboflavin in the pores. Optionally, the method further comprises (c) mixing the at least one particulate substrate having riboflavin entrapped in the pores thereof with a further solution of riboflavin for a time sufficient to permit the further solution of riboflavin to be absorbed into the pores of the at least one particulate substrate, and thereafter (d) removing unabsorbed liquid. Steps (c) and (d) may be repeated at least one time, for example, until all pores of the at least one particulate substrate are filled. Examples of useful particulate substrates include, but are not limited to, a polyamide, a polyacrylic acid or salt thereof, and an isoprene derivative. The polyamide may be nylon; the polyacrylic acid may be poly methyl methacrylate (PMMA) or polyhydroxyethyl methacrylate (pHEMA); and the isoprene derivative may be isoprene maleate polyethylene glycol (PEG).

Exemplary stable forms of riboflavin include, but are not limited to, riboflavin and HA; riboflavin and methylcellulose; riboflavin and nylon; riboflavin and PMMA; chlorophyll and HA; chlorophyll and methylcellulose; leucophor and HA; leucophor and methylcellulose; quinine and HA; quinine and methylcellulose; coumarin and HA; coumarin and methylcellulose; riboflavin, HA and nylon; riboflavin, HA and PMMA; riboflavin, methylcellulose and nylon; riboflavin, methylcellulose and PMMA; chlorophyll, HA and nylon; chlorophyll, HA and PMMA; chlorophyll, methylcellulose and nylon; chlorophyll, methylcellulose and PMMA; leucophor, HA and nylon; leucophor, HA and PMMA; leucophor, methylcellulose and nylon; leucophor, methylcellulose and PMMA; quinine, HA and nylon; quinine, HA and PMMA; quinine, methylcellulose and nylon; quinine, methylcellulose, and PMMA; coumarin, HA and nylon; coumarin, HA and PMMA; coumarin, methylcellulose and nylon; and coumarin, methylcellulose and PMMA. The skilled artisan would appreciate that the above is not an exhaustive list.

The invention is further illustrated by the following non-limiting examples.

EXAMPLES

Example 1

A Riboflavin-Hyaluronic acid complex was prepared according to the following procedure:
1. 200 mg of Riboflavin (available from DSM International) was added to 1979.8 g de-ionized water.
2. Using an overhead mixer, the Riboflavin was mixed until no particles were visible.
3. Hyaluronic acid (available from Actives International) was added very slowly (at about 0.5-1.0 g over 5-7 hours) with vigorous mixing until a total of 16 g was added.
4. 4.0 g of Optiphen (phenoxyethanol/caprylyl preservative) was then added with mixing until the batch was a homogeneous syrupy "gel".
5. The gel (having a concentration of 0.01% Riboflavin, 0.8% Hyaluronic acid, 0.2% Optiphen and 98.99% water) was separated into three glass baking pans and concentrated by evaporating water under vacuum in an oven at 85° C. for approximately 8 hours. The final concentration of the gel was calculated as 0.06% Riboflavin, 5.13% Hyaluronic Acid and 2% Optiphen and 92.81% water, as determined using gravimetric analysis.

Example 2

A treatment (oil-in-water emulsion) cream formulation according to the present invention was prepared as follows:

| | Cream | |
|---|---|---|
| Sequence | Ingredient | Weight Percent |
| 1 | purified water | 30.4507 |
| 1 | glycerin | 1.0000 |
| 1 | disodium EDTA | 0.1000 |
| 1 | caffeine | 0.2000 |
| 1 | whey protein | 0.5000 |
| 1 | sucrose | 2.0000 |
| 1 | sodium dehydroacetate | 0.1000 |
| 2 | purified water | 10.0000 |
| 2 | acrylates/C10-30 alkyl acrylate crosspolymer | 0.2000 |
| 3 | isostearyl neopentanoate | 1.5000 |
| 3 | hydrogenated polyisobutene | 3.5000 |
| 3 | dimethicone | 0.1500 |
| 3 | PEG-100 stearate | 0.7500 |
| 3 | cetearyl alcohol/glucoside | 5.0000 |
| 3 | squalane/*Hordeum vulgare* (barley) extract/*Triticum vulgare* (wheat germ) extract | 0.5000 |
| 3 | cholesterol | 0.1000 |
| 3 | stearic acid | 0.5000 |
| 3 | cetyl esters | 1.5000 |
| 3 | methylglucose sesquistearate | 0.8500 |
| 3 | cholesterol/potassium sulfate | 0.0500 |
| 3 | polyglyceryl-3 beeswax | 2.2000 |
| 3 | phytosphingosine | 0.2000 |
| 3 | polybutene | 2.0000 |
| 4 | phenyltrimethicone/Polysilicone-11 | 4.0000 |
| 5 | hyaluronic acid (1% SOL PF) | 10.0000 |
| 6 | aminomethyl propanol | 0.2000 |
| 7 | butylene glycol | 3.9000 |
| 7 | phenoxyethanol | 0.1700 |
| 7 | 1,2-hexanediol/caprylyl glycol | 0.3500 |
| 7 | purified water | 1.2300 |
| 7 | mica/titanium dioxide | 0.2500 |
| 7 | polymethyl methacrylate | 1.5000 |
| 7 | silica/green 5/polyurethane-40 | 1.0000 |
| 7 | mica/titanium dioxide/tin oxide | 3.0000 |
| 8 | *Camelia sinensis* (green tea) leaf extract/glycerin/water | 1.0000 |
| 8 | *Siegesbeckia orientalis* (St. Paulswort) extract/glycerin | 0.5000 |
| 8 | glyceryl polymethacrylate/PEG-8/palmitoyl oligopeptide | 1.0000 |
| 8 | Saccharomyces lysate extract/water | 0.2500 |
| 9 | riboflavin | 0.0083 |
| 9 | sodium hyaluronate | 0.6640 |
| 9 | phenoxyethanol/caprylyl glycol | 0.1670 |
| 9 | purified water | 7.4600 |
| TOTAL | | 100.0000 |

1. Sequence 1 ingredients were heated at 80° C. in the main kettle.
2. At the same time, sequence 2 ingredients were pre-mixed in an auxiliary kettle.
3. Sequence 2 ingredients were then added over the sequence 1 ingredients in the main kettle and mixed for 15 minutes at 80° C.
4. Sequence 3 ingredients were then pre-mixed at 80° C. then added to the main kettle and the batch mixed for 15 minutes at 80° C.
5. The batch was cooled to 60° C. prior to adding sequence 4 ingredient to the main kettle and the batch mixed for 15 minutes.

6. The batch was cooled down to 45° C., prior to adding the sequence 5 ingredient and then the sequence 6 ingredient, and the batch mixed and cooled to 40° C.
7. The sequence 7 ingredients were premixed in an auxiliary vessel until no powder settled to the bottom, and then added to the main kettle with mixing.
8. Sequence 8 ingredients were premixed in an auxiliary vessel, while the main kettle was cooled to 35° C.
9. Sequence 8 ingredients were the added to the main kettle with mixing.
10. Sequence 9 ingredients were premixed in an auxiliary vessel and then added to the main kettle at 35° C. with mixing
11. Mixing was stopped when the main kettle reached 35° C.

Example 3

A treatment solid stick (water-in-silicone) formulation according to the present invention was prepared as follows:

| Solid Stick | | |
| --- | --- | --- |
| Sequence | Ingredient | Weight Percent |
| 1 | isohexadecane | 5.9000 |
| 1 | oleic/linoleic/linolenic polyglyceride | 1.0000 |
| 1 | polyethylene | 3.0000 |
| 1 | polyethylene | 9.5000 |
| 1 | octyldodecanol | 4.5500 |
| 2 | polydiethylsiloxane | 3.0000 |
| 2 | nylon-12 | 2.5000 |
| 2 | cetearyl olivate/sorbitan olivate | 0.7500 |
| 2 | sodium polyacrylate/purified water | 0.0500 |
| 2 | *Helianthus annuus* (sunflower) seed wax | 2.5000 |
| 2 | mica/titanium dioxide | 0.2500 |
| 2 | polymethyl methacrylate | 1.5000 |
| 2 | silica/green 5/polyurethane | 1.0000 |
| 2 | mica/titanium dioxide/tin oxide | 3.0000 |
| 2 | isohexadecane | 3.6000 |
| 2 | neopentyl glycol diheptanoate | 10.2000 |
| 3 | cetyl PEG/PPG-10/1 dimethicone | 1.0000 |
| 3 | lauryl PEG-9 polydimethylsiloxyethyl dimethicone | 0.5000 |
| 3 | phytostearyl isostearate | 10.0000 |
| 3 | shea butter | 5.0000 |
| 3 | tricaprylin | 3.8000 |
| 3 | polyglyceryl-2 triisostearate | 4.8500 |
| 3 | bis-diglyceryl polyacyladipate-2 | 8.0000 |
| 4 | purified water | 5.2507 |
| 4 | caprylyl glycol/phenoxyethanol/hexylene glycol | 1.0000 |
| 4 | riboflavin | 0.0083 |
| 4 | sodium hyaluronate | 0.6640 |
| 5 | phenoxyethanol/caprylyl glycol | 0.1670 |
| 5 | purified water | 7.4600 |
| TOTAL | | 100.0000 |

1. Sequence 1 ingredients were added to the main beaker and heated to 85° C.
2. Each additional ingredient of sequences 2 and 3 was added one at a time with mixing to the main beaker.
3. Sequence 4 and 5 materials were premixed at 80° C., and then added to the main beaker.
4. The batch was mixed for 10 minutes and then poured into molds.

Example 4

The cream formulation of Example 2 and the stick formulation of Example 3 were analyzed for optical performance via an in-vitro testing method using photographs of a Caucasian woman with severity 8 dark under eye circles (based on a scale of 0 to 10; "0" indicating no apparent dark under eye circles (DUEC) and "10" indicating an extreme case of DUEC) printed on matte paper. For purposes of application to paper, water was first evaporated from the cream sample to prevent ink bleed. The residual formula sample was then added to the photograph as follows. Formula samples (0.01 gm.) were applied with a fingertip to one eye on separate photographs, while the other eye on each photograph was untreated. The stick sample was applied to the under eye areas on a separate photograph in the same manner as was done for the cream sample. The respective under eye areas were then analyzed for color and light output. Readings were taken with a Color Eye Spectrophotometer (GretagMacBeth®Coloreye®XTH) in reflection mode using standard default settings, and CIELAB mathematics, and analyzed by X-rite Color Control software which plots % reflection as a function of wavelength. The device is a diffuse reflectance spectrophotometer that works by flashing a known light source into a sphere that has an opening on one side. The light then bounces around the sphere and off the sample, eventually making its way to the detector. The detector then measures the light at specific wavelengths and calculates the percent reflectance of the sample. The percent reflectance can be used to examine what happens to light at specific wavelengths or calculate CIELAB color to incorporate a human response function into the measurements. The data is recorded at each wavelength as a percent reflectance. This data is then used to calculate CIELAB color. In order to calculate CIELAB the reflectance data is multiplied by the sensitivity curves of the cones in the human eye. In this way we incorporate how the human eye responds into the calculation and from the calculations we arrive at L*, a*, and b* values. L* represents the lightness-darkness scale (the higher the value, the lighter the result), a* represents the green-red component of light (the higher the value, the more red), and b* represents the blue-yellow component of light (the higher the value, the more yellow). Results are shown on the graph in FIG. 3. Pre-treatment and post-treatment measurements of the photographs were taken. The blue line on the graph corresponds to measurements taken of the untreated (left) under eye circle on the photograph. The red line on the graph corresponds to measurements taken of the (right) under eye circle to which the cream of Example 3 was applied. The purple line on the graph corresponds to measurements taken of the under eye area to which the stick formulation of Example 4 was applied. For reference, measurements of the cheek were also taken (green line).

Figure 3:
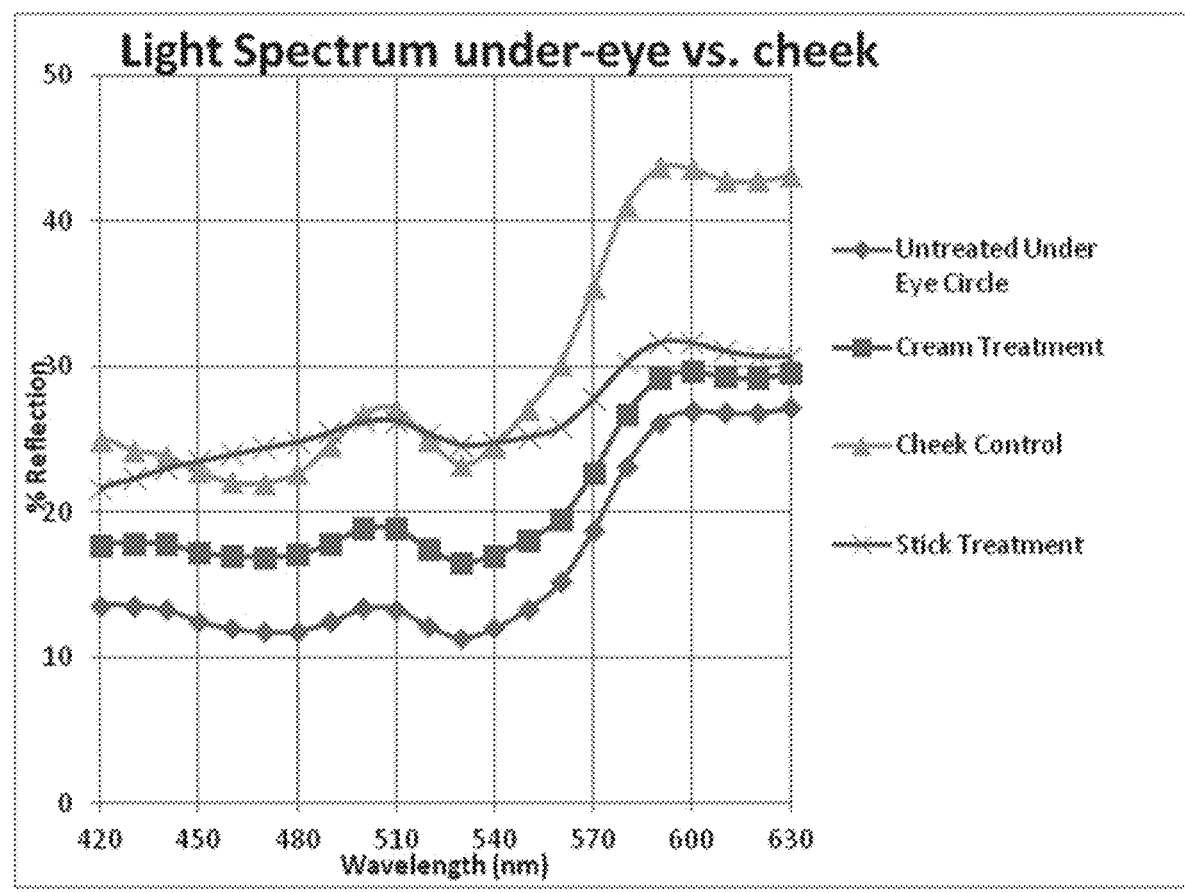
FIG. 3 is a graph indicating the change in total percent reflection of under eye and cheek areas after treatment of the under eye area with an optically-activated system according to the invention.

As demonstrated in FIG. 3, the total percent reflection, measured in RFUs (riboflavin reflection units) was increased over the range of 420 nm through 580 nm for the under eye circle treated with either the cream or the stick formulation of the invention compared with the untreated under eye circle. Moreover, both treatment formulations reduce the optical gap (the contrast) between the under eye area and the cheek adjacent the under eye area. Spectrophotometer color analysis of the photographs in FIG. 3 indicated an improvement in lightness value (L*), a reduction of redness value (a*) and a decrease in yellow value (b*). For example, before treatment with the cream product, L*=48.6, a*=17.89 and b*=11.07, while after treatment, L*=54.56, a*=9.26 and b*=9.05.

Figure 4:
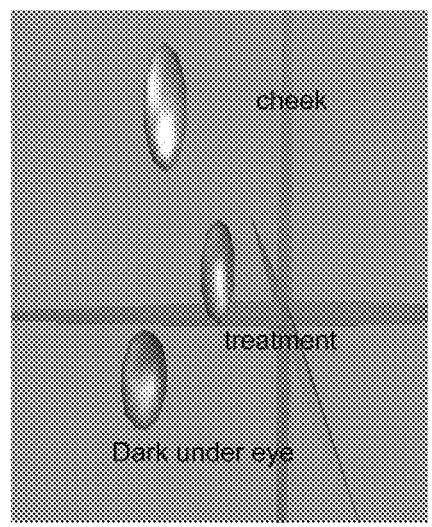
FIG. 4 is a schematic representation of a 3D spectrophotometer color analysis of the CIELab data obtained from FIG. 3.

FIG. 4 is a schematic representation of a 3D spectrophotometer color analysis of the CIELab data obtained from FIG. 2 indicating an improvement in lightness value (L*), a reduction of redness value (a*), and a decrease in yellow value (b*).

Example 5

The optical effects of a riboflavin-hyaluronic acid complex-containing optically-activated system according to the invention in the form of an anhydrous stick (Example 3) or in the form of a cream formulation (Example 2) on the appearance of DUEC were determined.

Twenty female volunteers who met the inclusion and exclusion criteria completed the study. The qualified panelists were those who were generally in good health and who exhibited moderate to severe levels of dark under eye circles (DUEC) as determined by an expert clinical grader. Females who were pregnant or lactating or who demonstrated serious dermatological concerns were excluded form participating in the study. Prior to the start of product application, the volunteers were asked to wash their faces. Thereafter, they each had their baseline pictures taken with the Visia-CR digital photography system (Canfield Scientific, Fairfield, N.J.); expert grading for their baseline DUEC score were also conducted. Then, the subjects received product treatments on their under eye regions. The stick (Example 3) and cream (Example 2) formulations were consistently applied on the left and right side of the face, respectively. The application was administered by a cosmetologist in order to control the application. Fifteen minutes after the treatments, additional Visia-CR pictures of the subjects were taken in a manner similar to that of the baseline. Another live expert grading was conducted, and the subjects were also asked if they perceived any improvements on their DUEC. These procedures were repeated after 60 and 120 minutes of application. After the last time point, the subjects' participation was concluded.

The digital photographs collected in the study were subsequently subjected to image analysis and expert photo grading. The digital images were used to extract L*, a* and b* values from the under eye and cheek regions of the face. Contrast values, defined as cheek minus under eye value, were calculated separately. The significance of the difference in the mean values of the time points and treatments was tested using one-way Repeated ANOVA, the significance level being set at 0.05.

Figure 5A:
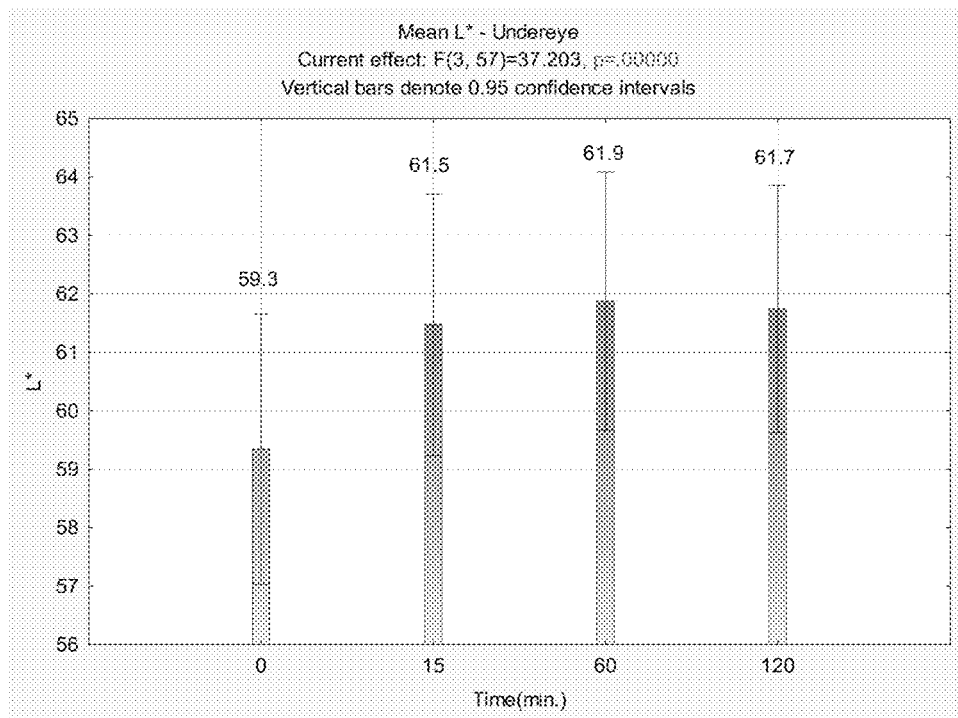
FIGS. 5a, 5b and 5c are bar graphs showing the mean lightness scale (L*) values of the under eye area, the cheek area and contrast between the under eye and cheek areas after treatment with an anhydrous stick formulation of the invention.
Figure 5B:
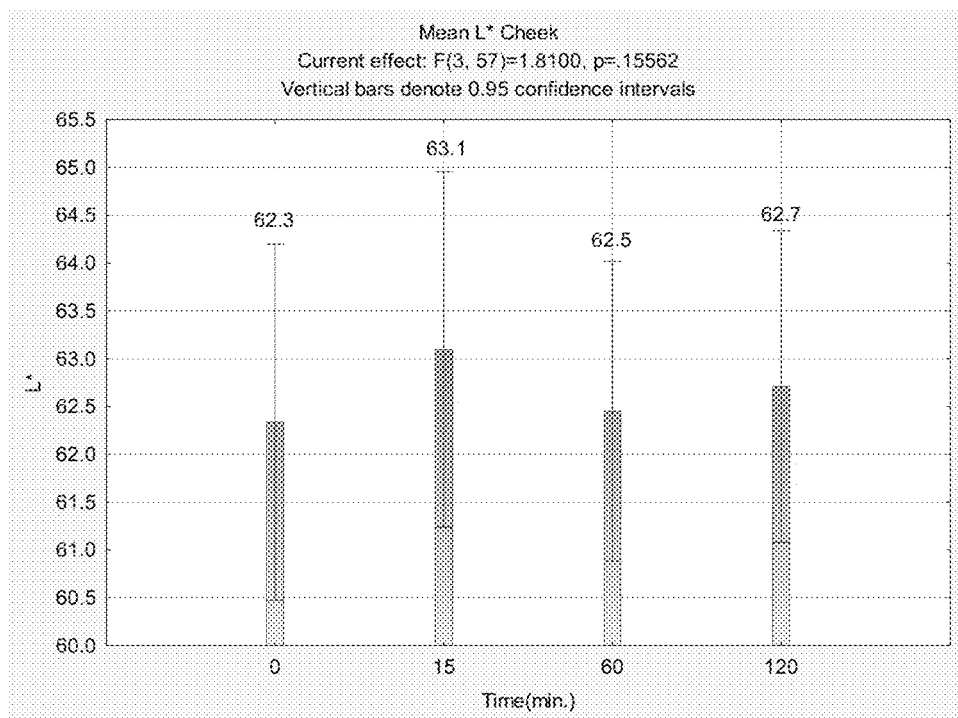
Figure 5C:
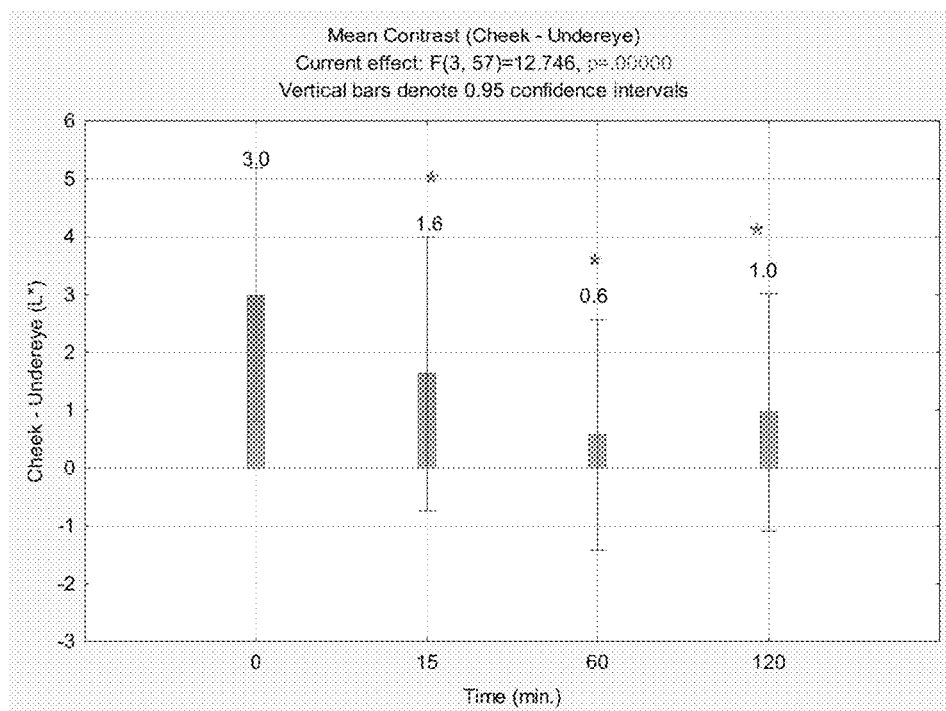

FIG. 5 shows the mean L* values of the under eye (FIG. 5a), the cheek (FIG. 5b), and the contrast between the under eye and cheek areas (FIG. 5c) after treatment with an anhydrous stick formulation according to the present invention. The results indicate that there was a significant increase of L* on the under eye area (FIG. 5a) indicating that the appearance of the treated skin was lightened. The effect remained significant even two hours after the application of the product to the under eye area. This effect was not observed on the untreated cheek area (FIG. 5b). As shown in FIG. 5c, treatment with the stick product also significantly reduced the contrast between the under eye and the cheek areas which contributed to the overall lightened appearance of the treated under eye region up to two hours after application of the product to the skin under the eye.

Figure 6A:
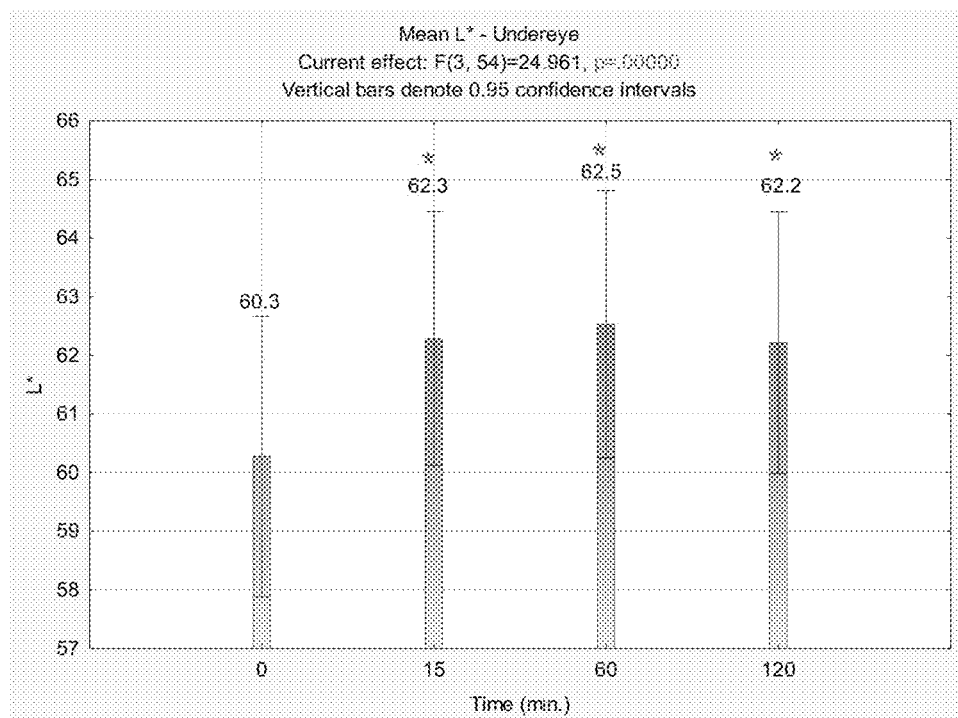
FIGS. 6a, 6b and 6c are bar graphs showing the mean L* values of the under eye area, the cheek area and contrast between the under eye and cheek areas after treatment with a cream formulation of the invention.
Figure 6B:
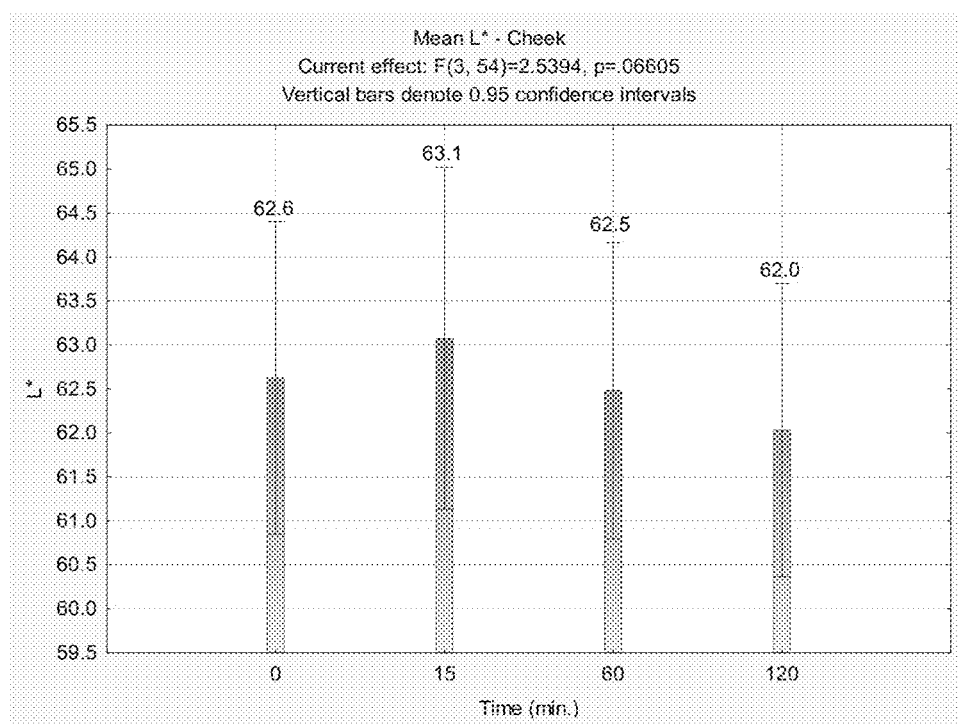
Figure 6C:
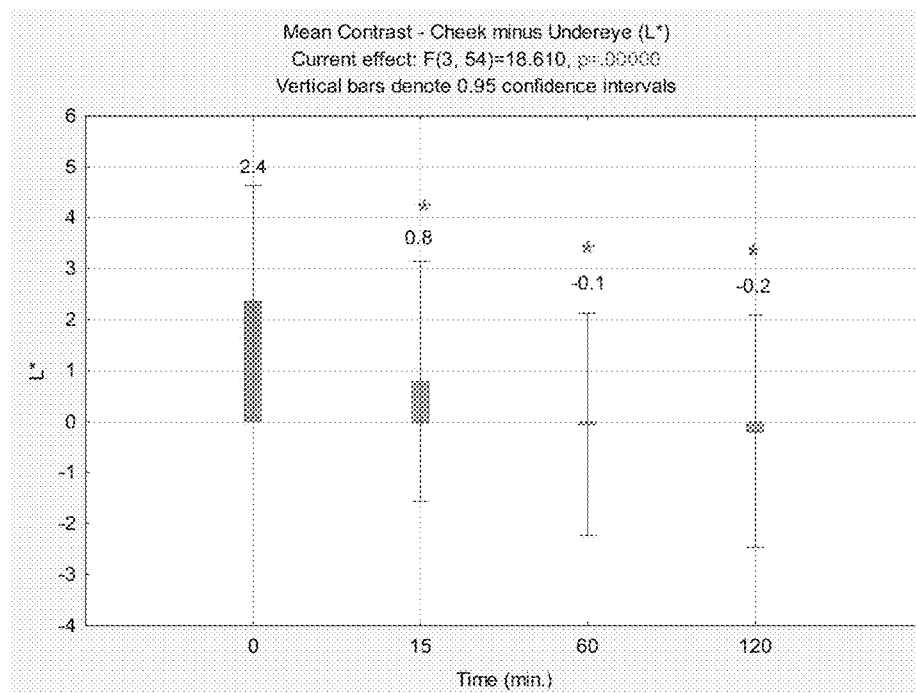

FIG. 6 shows the mean L* values of the under eye (FIG. 6a), cheek (FIG. 6b), and contrast between the under eye and cheek areas (FIG. 6c) after treatment of the under eye with a cream product according to the invention. A significant increase of L* was observed for the under eye region (FIG. 6a) indicating that the product lightened the appearance of the skin under the treated eye. The effect remained significant even two hours after application of the product to the under eye area. This effect was not observed on the untreated cheek area (FIG. 6b). The lightening effect of product treatment significantly reduced the contrast between the under eye and the cheek areas which contributed to the overall lightened appearance of the treated under eye region up to two hours after application of the product to the skin under the eye (FIG. 6c).

Figure 7A:
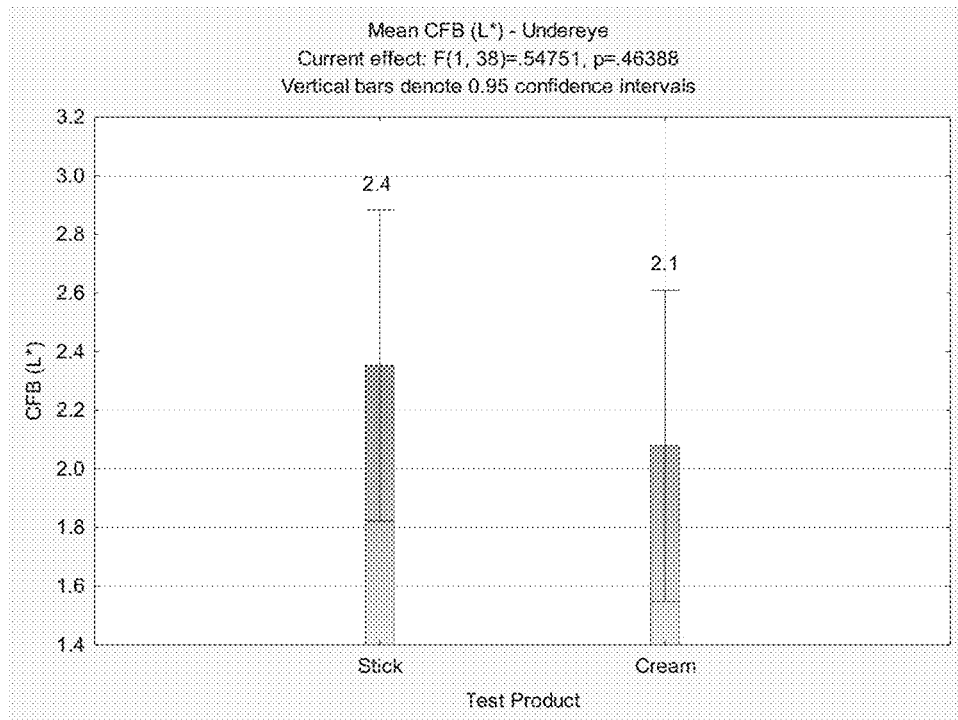
FIGS. 7a, 7b and 7c are bar graphs showing the mean change-from-baseline of the L* values of the under eye area, the cheek area and contrast between the under eye and cheek areas after treatment with cream and stick formulations of the invention.
Figure 7B:
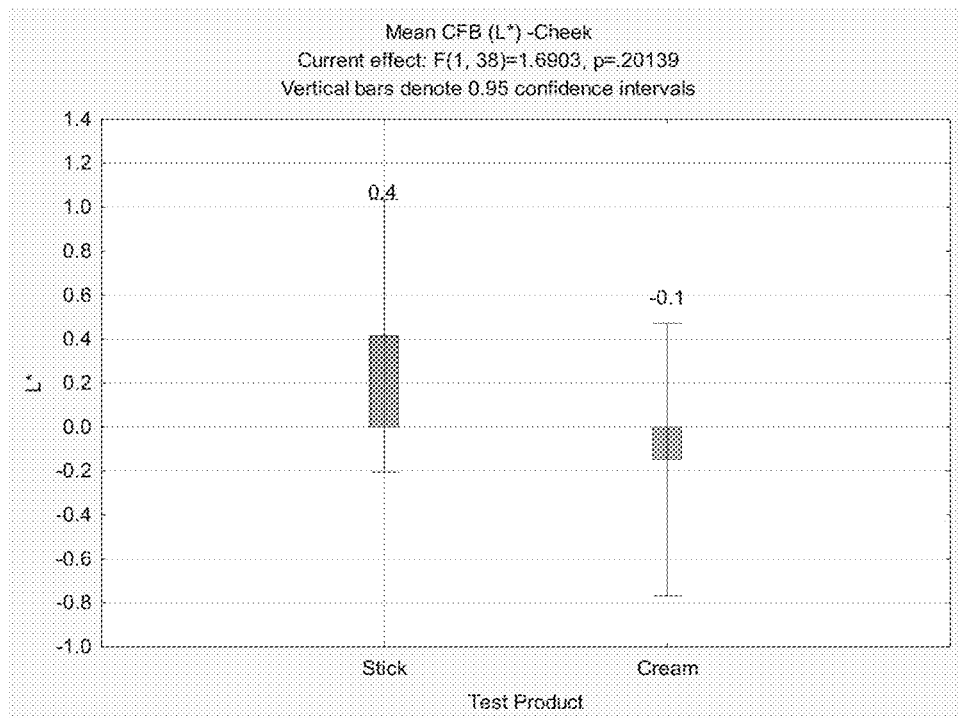
Figure 7C:
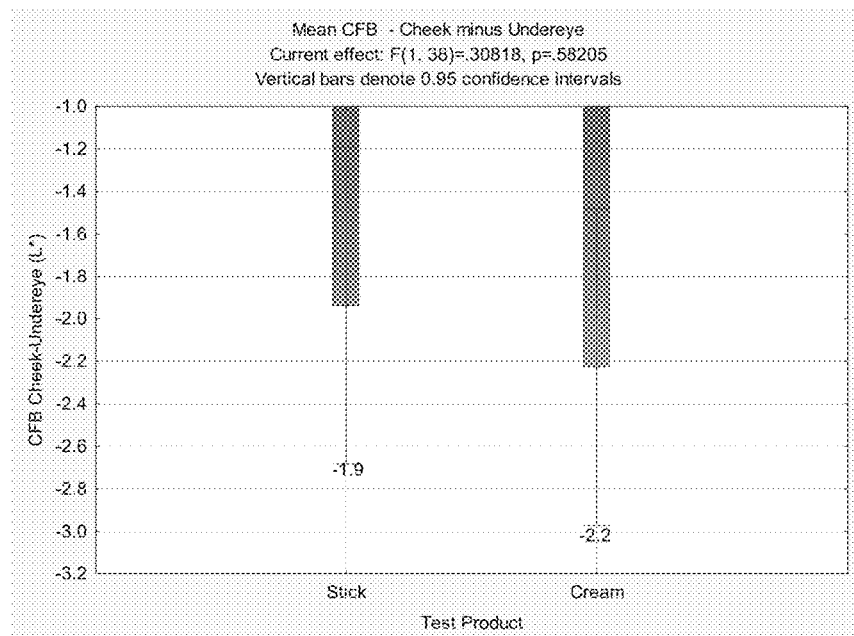

FIG. 7 shows the mean change-from-baseline of the under eye (FIG. 7a), cheek (FIG. 7b) and contrast between under eye and cheek regions (FIG. 7c) after treatment with the cream and stick products. A similar improvement effect (not significantly different) was observed after treatment with each product on under eye lightness and contrast.

Figure 8A:
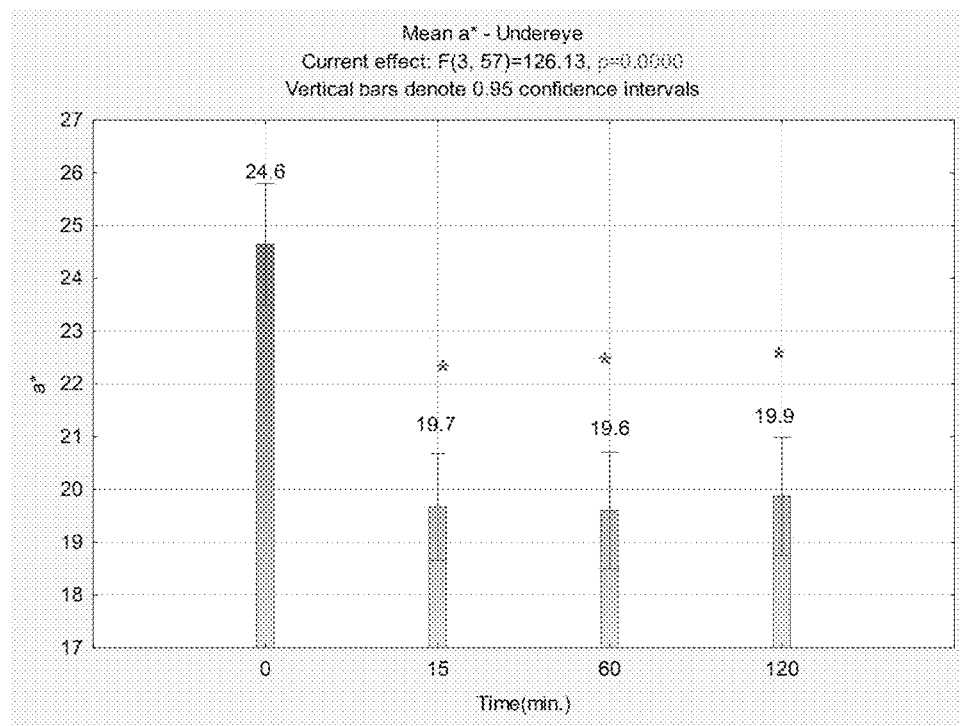
FIGS. 8a and 8b are bar graphs showing the mean red-green scale (a*) values of the under eye and cheek areas after treatment with an anhydrous stick formulation of the invention.
Figure 8B:
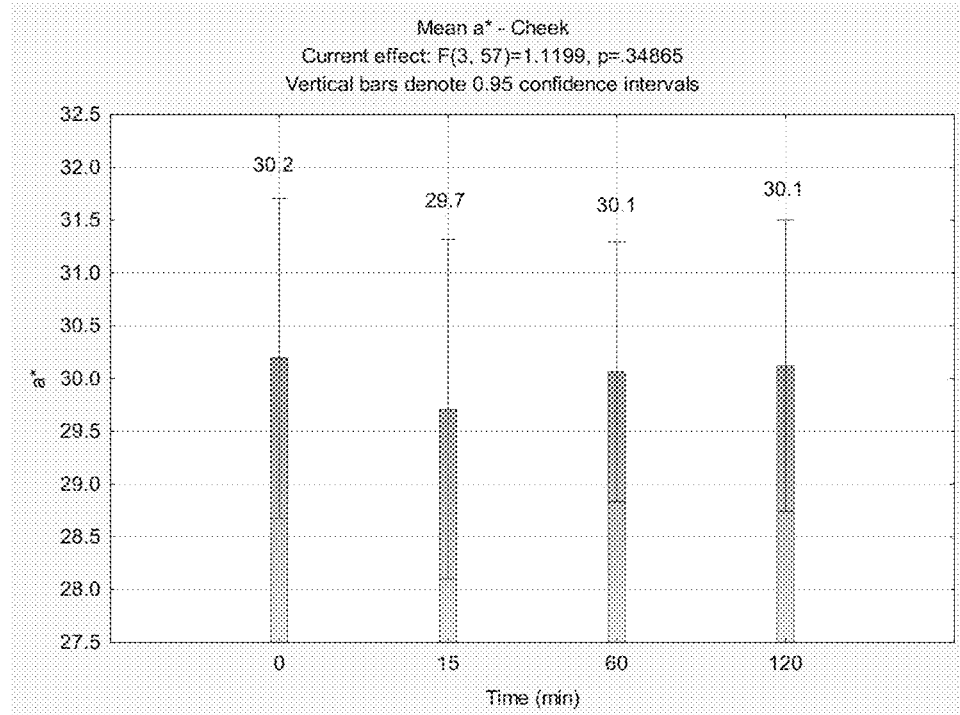

FIG. 8 shows the mean a* values of the under eye (FIG. 8a) and cheek (FIG. 8b) regions after treatment with the stick product. A significant decrease in a* was observed for the under eye area (FIG. 8a) corresponding to an increase in greenness appearance of the skin due to the light compensation in the green component of light contributed by the riboflavin in the product. This effect remained significant even two hours after application of the product to the under eye area. This effect was not observed for the untreated cheek area (FIG. 8b).

Figure 9A:
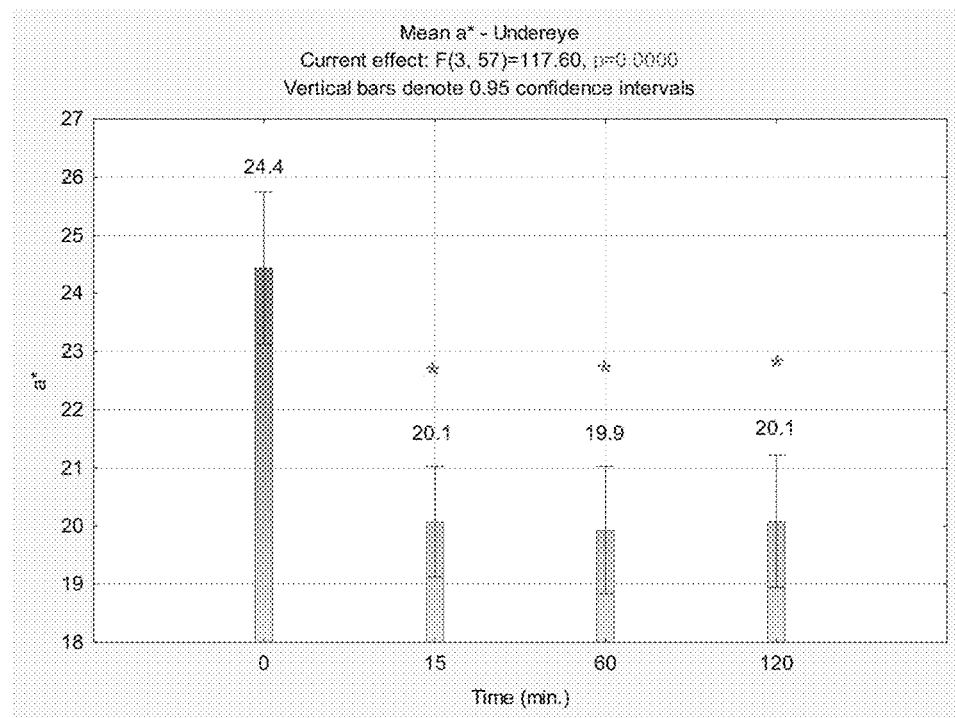
FIGS. 9a and 9b are bar graphs showing the mean a* values of the under eye and cheek areas after treatment with a cream formulation of the invention.
Figure 9B:
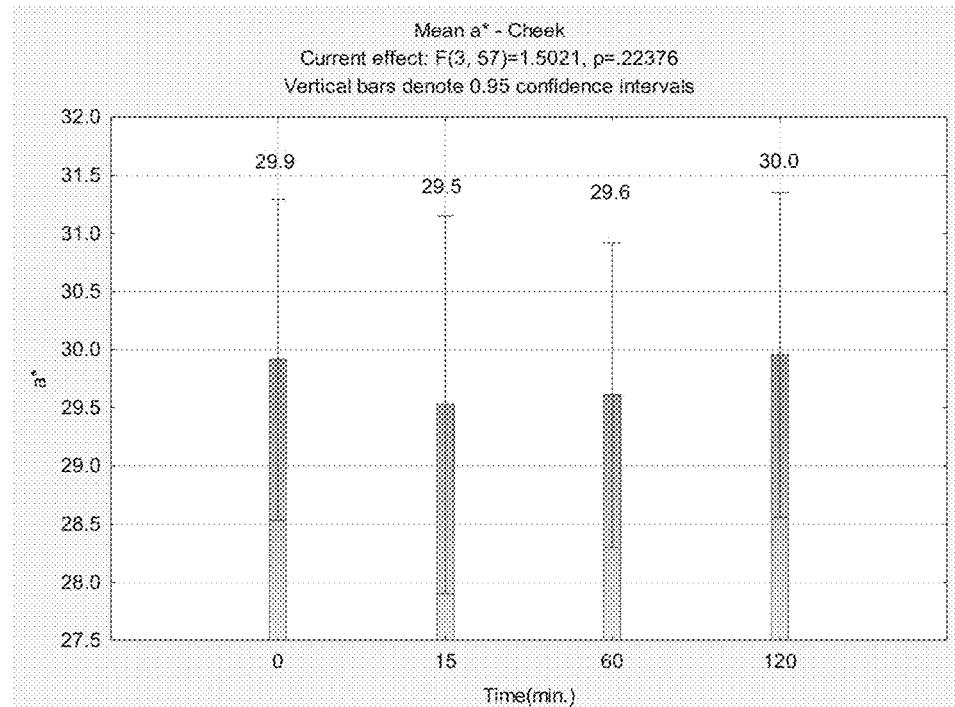

FIG. 9 shows the mean a* values of the under eye (FIG. 9a) and cheek (FIG. 9b) after treatment with the cream product. Similar to the results observed using the stick product, there was a significant decrease of a* on the under eye region (FIG. 9a), demonstrating an increase in greenness of the skin after treatment with the cream product due to the contribution of the green component of light by the riboflavin in the product. This effect remained significant even two hours after application of the cream product to the under eye area. This effect was not observed on the untreated cheek region (FIG. 9b).

Figure 10A:
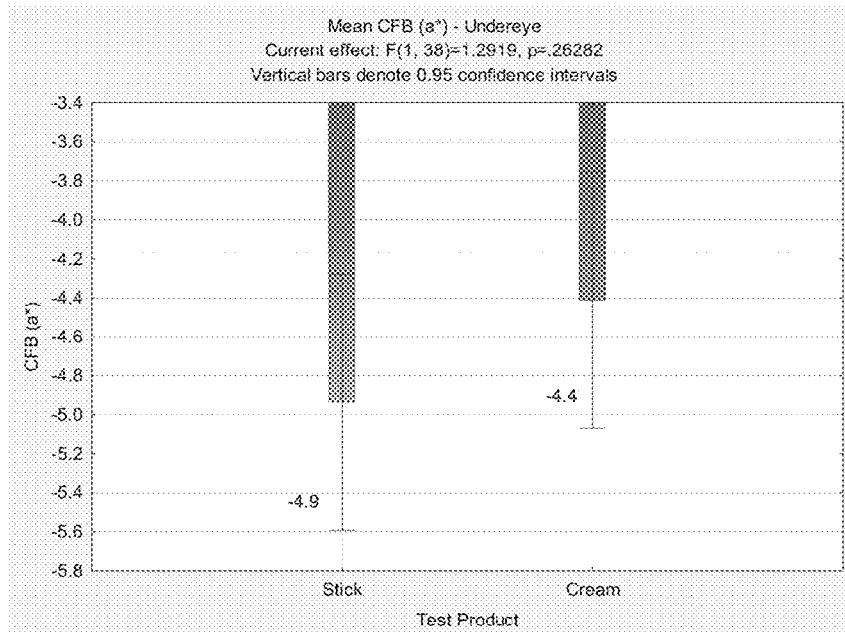
FIGS. 10a and 10b are bar graphs showing the mean change-from-baseline of the a* values of the under eye and cheek areas after treatment with cream and stick formulations of the invention.
Figure 10B:
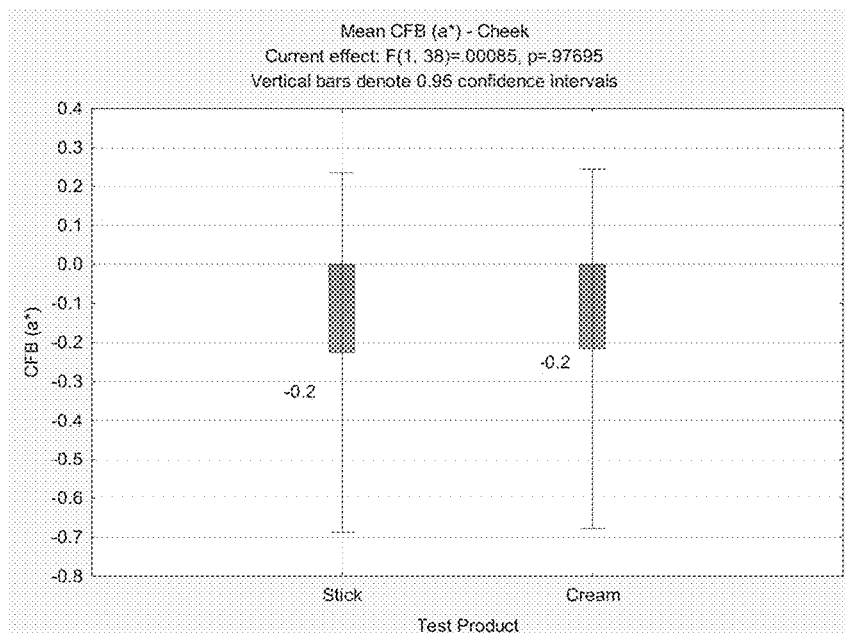

FIG. 10 shows the mean change-from-baseline of the a* values of the under eye (FIG. 10a) and cheek (FIG. 10b) areas after treatment with the stick or cream formulations. Both products resulted in similar improvement (not significantly different) effects on the dark under eye area.

Figure 11A:
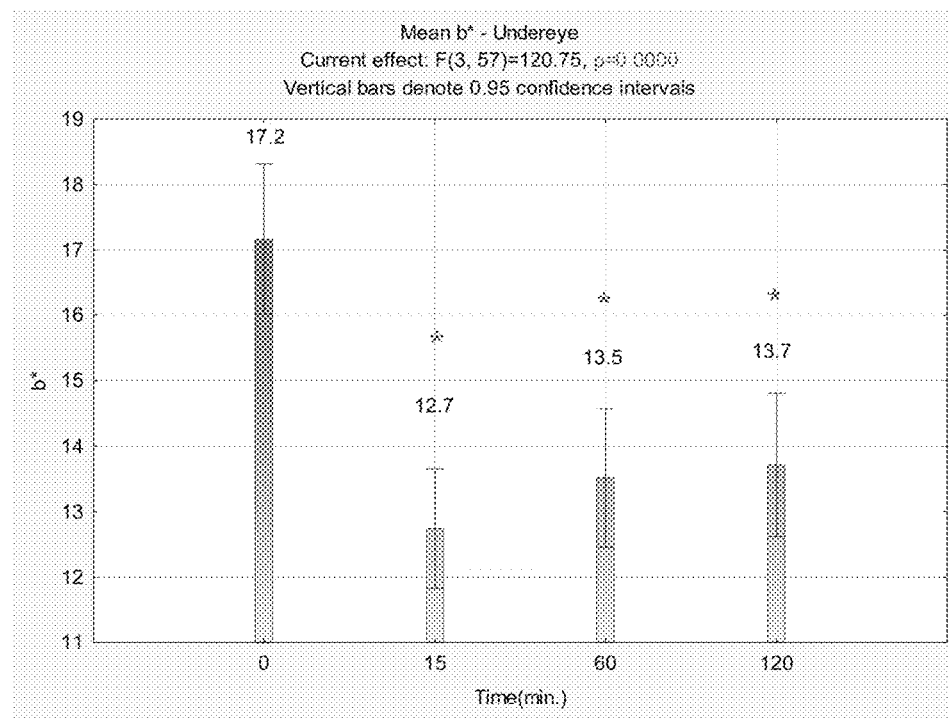
FIGS. 11a and 11b are bar graphs showing the mean yellow-blue scale (b*) values of the under eye and cheek areas after treatment with an anhydrous stick formulation of the invention.
Figure 11B:
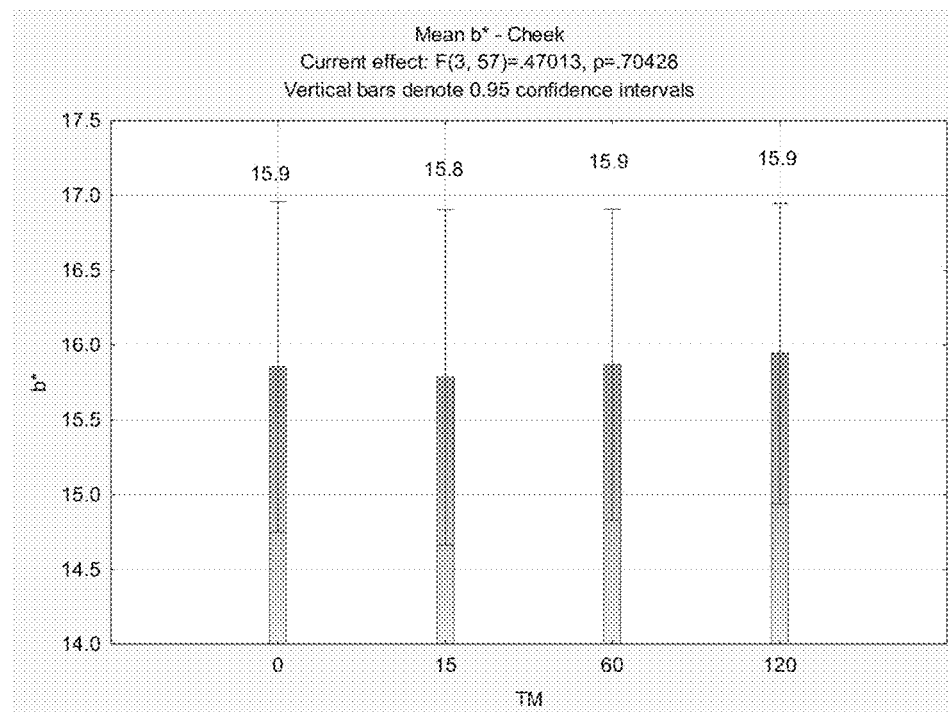

FIG. 11 shows the mean b* values of the under eye (FIG. 11a) and cheek (FIG. 11b) areas after treatment with the stick product. There was a significant decrease in b* observed on the under eye region (FIG. 11a) which correlated with a decrease in yellowness of the treated skin due to the overall lightening effect of the product containing the riboflavin. This effect remained significant even two hours after application of the product to the skin of the under eye. This effect was not observed on the untreated cheek region (FIG. 11b).

Figure 12A:
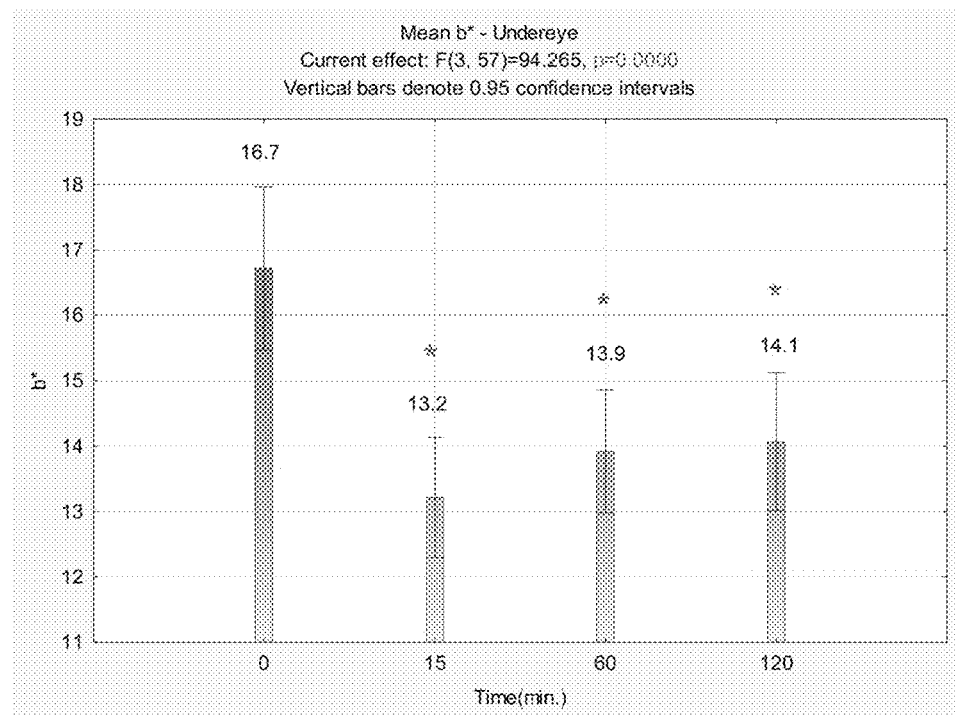
FIGS. 12a and 12b are bar graphs showing the mean b* values of the under eye and cheek areas after treatment with a cream formulation of the invention.
Figure 12B:
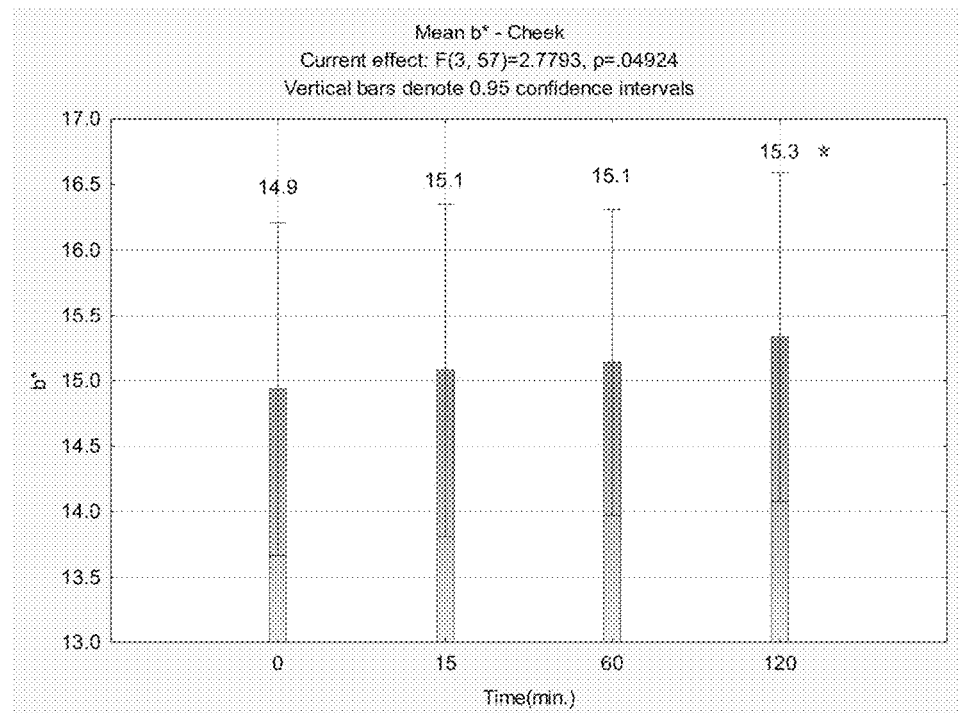

FIG. 12 shows the mean b* values of the under eye (FIG. 12a) and cheek (FIG. 12b) regions after treatment of the under eye region with the cream product. There was a significant decrease in b* observed on the under eye (FIG. 12a) region which correlated with a decrease in the yellowness of the treated skin due to the overall lightening effect imparted by the riboflavin in the product.

Figure 13A:
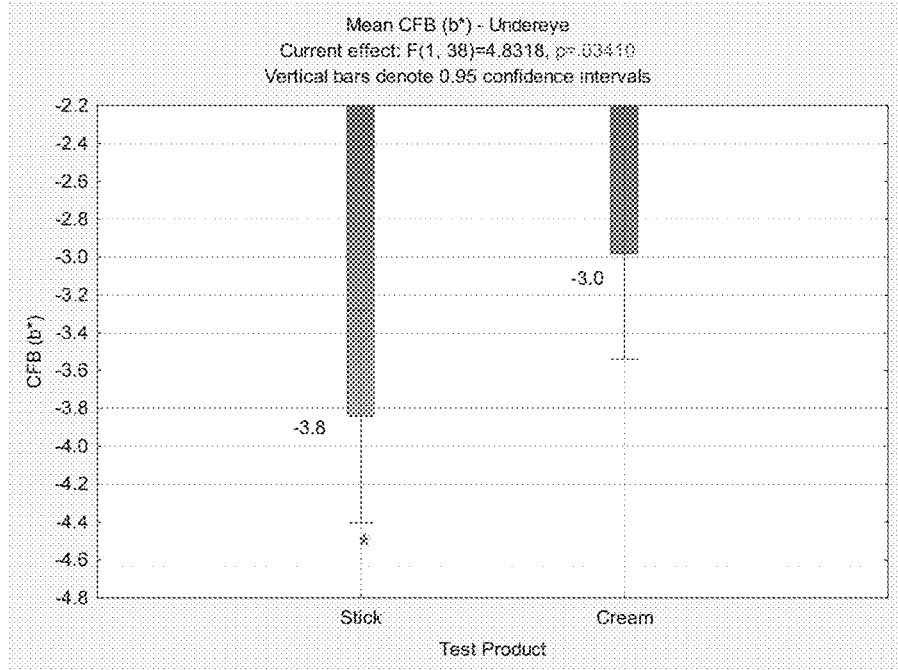
FIGS. 13a and 13b are bar graphs showing the mean change-from-baseline of the b* values of the under eye and cheek areas after treatment with the stick and cream formulations.
Figure 13B:
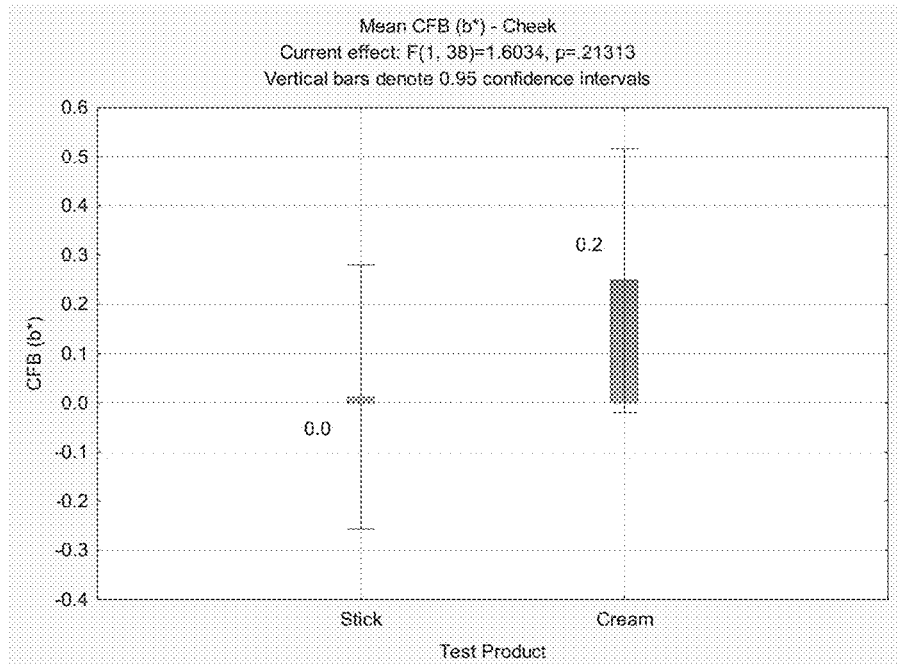

FIG. 13 shows the mean change-from-baseline of the b* values of the under eye (FIG. 13a) and cheek (FIG. 13b) regions for both the stick and cream product formulations.

The b* value observed after treatment with the stick product was significantly lower than the b* value observed after treatment with the cream product on the under eye region (FIG. 13a) indicating that the stick product imparted more blue reflection to the skin correlating with a decrease in yellowness.

Based on the results of the analysis of the L*, a*, and b* components of digital images, both the stick and cream formulations containing the optically-activated systems of the present invention significantly increased the appearance of lightness of the DUEC, significantly decreased the lightness contrast between the under eye and the cheek areas, significantly increased the greenness of the DUEC, and significantly decreased the yellowness of the DUEC. The performances of the two product formulations were not significantly different from each other with the exception of the b* value on the under eye region where the stick was observed to provide a significantly greater decrease in yellowness of the skin compared with the cream formulation. It is believed that the appearance of DUEC was significantly improved as a result of the presence of the riboflavin in the products which absorbed and reflected green and blue light, compensating for the lack of greenness and blueness in the skin of the DUEC and increasing the lightness overall.

Example 6

A series of fluorescent compound-substrate complexes was prepared as follows:
6.1. A complex comprising a riboflavin-hyaluronic acid (HA) gel was prepared according to the following procedure:
 a. 200 mg of riboflavin (available from DSM International) was added to 1979.8 g de-ionized water.
 b. Using an overhead mixer, the riboflavin was mixed until no particles were visible.
 c. HA (available from Actives International) was added very slowly (at about 0.5-1.0 g over 5-7 hours) to the riboflavin solution with vigorous mixing until a total of 16 g was added.
6.2. A complex comprising a riboflavin-HA gel entrapped in nylon (Orgasol) was prepared according to the following procedure:
 a. 100 g of the riboflavin-HA complex prepared in 6.1 was mixed with 100 g of Orgasol 2002 NAT COS (available from Atofina Company).
 b. Water was removed by heating to 80° C. under vacuum.
 c. A soft light yellow powder was obtained. The powder had a riboflavin content of 5 mg.
 d. A sample of the powder mixed with glycerin (10% powder/90% glycerin) was submitted for spectrophotometric analysis.
6.3. A complex comprising riboflavin-HA gel entrapped in PolyMethylMethacrylate (PMMA) was prepared according to the following procedure:
 a. 100 g of the riboflavin-HA complex prepared in 6.1 was mixed with 100 g of PMMA Microspheres M (available from Matsumoto Company).
 b. Water was removed by heating to 80° C. under vacuum.
 c. A soft light yellow powder was obtained. The powder had a riboflavin content of 5 mg.
 d. A sample of the powder mixed with glycerin (10% powder/90% glycerin) was submitted for spectrophotometric analysis.
6.4. A complex comprising a riboflavin-methylcellulose gel was prepared according to the following procedure:
 a. 200 mg of riboflavin was added to 1979.8 g de-ionized water.
 b. Using an overhead mixer, the riboflavin was mixed until no particles were visible.
 c. Methylcellulose (available from Dow Chemical as Methocel K4M) was added very slowly (at about 0.5-1.0 g over 5-7 hours) to the riboflavin solution with vigorous mixing until a total of 16 g was added.
6.5. The following gel complexes (each containing 0.01% fluorophor) were prepared in accordance with the procedure in 6.1, above:
 a. Leucophor-HA
 b. Chlorophyll-HA
 c. Coumarin-HA
 d. Quinine-HA
The following gel complex was made in accordance with the procedure in 6.4, above:
 e. riboflavin-methylcellulose
Samples of the soft light yellow powders thus-obtained were mixed with glycerin and submitted for spectrophotometric analysis.
6.6 A complex comprising riboflavin-PMMA was made in accordance with the following procedure:
 a. A riboflavin solution was prepared by adding 200 mg of riboflavin in 1999.8 g of de-ionized water and mixing using an overhead mixer until no particles of riboflavin were visible.
 b. 100 g of the riboflavin solution made in step a were mixed with 100 g of PMMA Microspheres M.
 c. Water was removed by heating to 80° C. under vacuum.
 d. A soft light yellow powder, having a riboflavin content of 5 mg, was obtained.
 e. A sample of the powder mixed with glycerin (10% powder/90% glycerin) was submitted for spectrophotometric analysis.
6.7 A complex comprising riboflavin-Orgasol was prepared in accordance with the following procedure:
 a. A riboflavin solution was prepared by adding 200 mg of riboflavin in 1999.8 g of de-ionized water and mixing using an overhead mixer until no particles of riboflavin were visible.
 b. 100 g of the riboflavin solution of step a were mixed with 100 g of Orgasol 2002 NAT COS.
 c. Water was removed by heating to 80° C. under vacuum; the riboflavin-Orgasol complex had a riboflavin content of 5 mg.
 d. A further 100 g of riboflavin solution of step a were mixed with 100.05 g of the riboflavin-Orgasol complex of step c.
 e. Water was removed by heating to 80° C. under vacuum; the riboflavin-Orgasol complex had a riboflavin content of 10 mg.
 f. A further 100 g of riboflavin solution of step a were mixed with 100.1 g of the riboflavin-Orgasol complex of step e.
 g. Water was removed by heating to 80° C. under vacuum; the riboflavin-Orgasol complex had a riboflavin content of 15 mg.
 h. A sample of the soft light yellow powder obtained in step g, mixed with glycerin (10% powder/90% glycerin) was submitted for spectrophotometric analysis.
6.8 A mixture comprising riboflavin-HA-Orgasol complex together with reflective pigments was prepared in accordance with the following procedure:
 a. A Riboflavin-HA-Orgasol complex was prepared as in 6.2 (resulting in a soft light yellow powder with a riboflavin content of 5 mg).
 b. The complex of step a was mixed with KTZ green (available from KOBO Company) and Chronosphere Opticals Brite Z1KG (available from Alzo/Arch Company) in glycerin (10% complex, 3% KTZ green, 1% Chronosphere Opticals Brite Z1KG, 86% glycerin).
c. The mixture prepared in step b was submitted for spectrophotometric analysis.

6.9 A complex comprising riboflavin-Orgasol was made according to the following procedure:
a. A riboflavin solution was prepared by adding 200 mg of riboflavin in 1999.8 g of de-ionized water and mixing using an overhead mixer until no particles of riboflavin were visible.
b. 100 g of the riboflavin solution prepared in step a were mixed with 100 g of Orgasol 2002 NAT COS.
c. Water was removed by heating to 80° C. under vacuum resulting in a riboflavin-Orgasol complex having a riboflavin content of 5 mg.
d. A further 100 g of the riboflavin solution prepared in step a were mixed with 100.05 g of the riboflavin-Orgasol complex of step c.
e. Water was removed by heating to 80° C. under vacuum.
f. A soft light yellow powder, having a riboflavin content of 10 mg was obtained.
g. A sample of the powder obtained in step f was mixed with glycerin (10% powder/90% glycerin) was submitted for spectrophotometric analysis.

Results of Example 6 are shown in Table 2, below.

TABLE 2

| Sample | L* | a* | b* | dE# |
| --- | --- | --- | --- | --- |
| 6.1 | 89.56 | 1.52 | 7.63 | NA |
| 6.2 | 91.50 | −4.8 | 16.97 | 8.37 |
| 6.3 | 90.09 | −1.45 | 8.20 | 5.24 |
| 6.5a | 92.26 | −0.94 | 4.09 | 17.59 |
| 6.5b | 87.83 | −6.89 | 11.73 | 14.99 |
| 6.5c | 92.27 | −2.94 | 7.76 | 16.16 |
| 6.5d | 92.13 | −1.43 | 5.10 | 17.17 |
| 6.5e | 89.44 | −7.66 | 47.66 | 0.08+ |
| 6.6 | 90.03 | −1.02 | 5.77 | 6.84 |
| 6.7 | 89.48 | −7.19 | 34.90 | 25.88 |
| 6.8 | 90.20 | −7.39 | 33.85 | 6.62 |
| 6.9 | 90.89 | −6.22 | 22.09 | 14.02 | dE represents the overall color shift. A value of at least about 2 corresponds to a human perception of a "just noticeable difference". The greater the value of dE, the more noticeable the color shift from baseline (Sample 6.1).
+with the exception of this value, all results in Table 2 are statistically significant compared with the baseline values (Sample 6.1).

As shown in Table 2, for Samples 6.1-6.3, 6.5(a-e), gel complexes were formed from various fluorescent compounds and substrates.

As discussed hereinabove, riboflavin had previously been known to fluoresce only in solution, but not in its particulate form. Surprisingly, however, it has been discovered that forming a complex between riboflavin and a substrate for the riboflavin (as herein defined) stabilizes the riboflavin against sensitivity to degradation by light and also against dissociation in aqueous media. Additionally, the L*, a* and b* values in Sample 6.1, demonstrate an illuminating radiant effect as the riboflavin in the complex continues to fluoresce yellowish-green after absorption of ambient light. This illuminating effect is particularly useful in camouflaging the appearance of, for example, fine lines, wrinkles, enlarged pores and cellulite. The color shift is useful for camouflaging DUEC and reducing skin redness.

For Samples 6.2 and 6.3, the riboflavin-HA complex is combined with a further, particulate, substrate, Orgasol or PMMA, respectively. Orgasol and PMMA contribute different optical properties to the respective complexes. The respective overall color shifts of the riboflavin-Orgasol and riboflavin-PMMA powder complexes compared to baseline are significantly increased. Each of the substrates contributes an enhanced greenness component and an equivalent or enhanced yellowness component to the emitted light, compared with baseline values, which is useful in addressing the appearance of dark under eye circles, rosacea, and other skin discolorations.

It is observed for Samples 6.5(a-e) that each of the complexes not only demonstrates fluorescence, but that each of the substrates contributes different optical properties to the respective complexes. All of the complexes demonstrate an enhanced green component of the emitted light compared with baseline.

For Sample 6.6, a complex is formed by mixing a solution of riboflavin with a particulate substrate. The green component of the light emitted is enhanced over the baseline value.

A comparison of Samples 6.7, 6.9 and 6.2 confirms that the amount of fluorescence emitted by the fluorescent compound in the complex is concentration dependent. Samples 6.2, 6.7 and 6.9 have riboflavin contents of 5 mg, 10 mg and 15 mg, respectively. Sample 6.7 demonstrates enhanced greenness and yellowness of the light emitted and enhanced overall color shift values (a*, b* and dE, respectively) compared with Sample 6.2. Sample 6.9 demonstrates enhanced greenness and yellowness of the light emitted and enhanced overall color shift values (a*, b* and dE, respectively) compared with Sample 6.7.

The presence of optically-reflective and/or light scattering materials of Sample 6.8 enhances the a* and b* values (increased green and yellow components of emitted light) compared with the light emitted by the complex of Sample 6.2. Additionally, Sample 6.8, with only 5 mg of riboflavin demonstrates similar L*, a* and b* values to Sample 6.7 having a riboflavin content of 15 mg. The dE value of Sample 6.8, due its greater riboflavin content and therefore, stronger fluorescent emission, is greater than the dE value of Sample 6.8.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of stabilizing riboflavin against degradation upon exposure to UV light by (a) mixing a hyaluronic acid substrate with a solution of riboflavin, and (b) evaporating the liquid to form an optically-activated complex in the form of a gel that will absorb light in the wavelength range of 260 to 460 nm and emit light in the wavelength range of 470 to 650 nm.

2. The method of claim 1, wherein the at least one substrate further comprises at least one particulate substrate, and the method further comprises (c) mixing the gel thus-produced with the at least one particulate substrate for a time sufficient to permit the gel to be absorbed into pores of the at least one particulate substrate, and thereafter (d) removing nonabsorbed liquid.

3. The method of claim 2, wherein the at least one particulate substrate is selected from a polyamide; a polyacrylic acid or a salt thereof; and an isoprene derivative.

4. The method of claim 1, wherein the riboflavin is present in the gel in amounts in the range of from about 0.001% to about 2%, by total weight of the g.

5. The method of claim 4, wherein the at least one substrate for the riboflavin is present in the gel in amounts in the range of from about 0.05% to about 25%, by total weight of the gel.

6. A stable form of riboflavin produced by the method of claim 1.

7. A stable form of riboflavin produced by the method of claim 2.

* * * * *